United States Patent [19]
Watanabe et al.

[11] Patent Number: 5,180,743
[45] Date of Patent: Jan. 19, 1993

[54] ANTI-INFLAMMATORY AND ANALGESIC COMPOUNDS, RELATED COMPOSITIONS AND METHODS FOR PREPARATION AND USE THEREOF

[75] Inventors: Kazuo Watanabe; Toshio Tuchida, both of Shiga, Japan; Duane R. Schultz, Miami, Fla.

[73] Assignees: Xonex Laboratories, Inc., Coral Gables, Fla.; Toyobo Co., Ltd., Osaka, Japan

[21] Appl. No.: 530,124

[22] Filed: May 29, 1990

Related U.S. Application Data

[63] Continuation-in-part of Ser. No. 252,207, Sep. 30, 1988, abandoned.

[51] Int. Cl.$^5$ ............................................. A61K 31/195
[52] U.S. Cl. .................................... 514/565; 514/673; 424/663; 424/664; 424/665; 424/583
[58] Field of Search ............... 424/583, 664, 665, 663; 514/2, 21, 825, 561, 565, 673; 530/858

[56] References Cited

U.S. PATENT DOCUMENTS 4,247,540  1/1981  Holtzmann ........................ 424/538

OTHER PUBLICATIONS

Hink et al. Inflammation 13(2): 175-184 (1989).
Skoog et al. Fundamentals of Analytical Chemistry, 1963 Holt, Rhinehart & Winston, New York pp. 668-669.
Byrnes et al. Clin Res 33(2): Abstr. 590A (1985).

*Primary Examiner*—Douglas W. Robinson
*Assistant Examiner*—Jean C. Witz
*Attorney, Agent, or Firm*—Pennie & Edmonds

[57] ABSTRACT

This application relates to an anti-inflammatory, immunosuppressive and analgesic composition, a method for its preparation, a pharmaceutical composition including it and a method of treating auto-immune diseases. The anti-inflammatory, immunosuppressive and analgesic compound is derived from ant venom extract which has been purified of contamination by a variety of non-active components present in crude ant venom extracts. A synthetic venom has also been prepared from various components. The related pharmaceutical composition has been shown to be effective in treating and alleviating the symptoms of auto-immune diseases, particularly rheumatoid arthritis.

9 Claims, 5 Drawing Sheets

ANTI-INFLAMMATORY AND ANALGESIC COMPOUNDS, RELATED COMPOSITIONS AND METHODS FOR PREPARATION AND USE THEREOF

RELATED APPLICATIONS

This application is a continuation-in-part of copending U.S. patent Ser. No. 252,207, filed Sep. 30, 1988.

BACKGROUND OF THE INVENTION

Venom Extracts

The biological activity of the crude extracts of the venom of stinging insects has been investigated for well over the last hundred years. Indeed, the first venom of ant to be partially chemically characterized was done so in the 17th century. In that study formic acid was distilled from the ants *Formica rufa*. Treatment regimes utilizing crude venom extracts (e.g., bee venom), have been reported for the treatment of rheumatoid arthritis. Bee venom has been reported for a treatment of rheumatism in United Kingdom Patent 425,543 issued Mar. 30, 1935; U.S. Pat. No. 2,112,828 issued Aug. 5, 1938 and U.S. Pat. No. 2,154,934 issued Apr. 18, 1939. Typically, however, these treatments have failed to produce noticeable or consistent effects due to the lack of purity of the venom extract and the lack of reproducibility of the venom extract compositions. In addition, since individual insects typically have small amounts of venom present the treatment regimes utilizing venom extracts were prohibitively expensive.

The biological activity of ant species has also been reported in the literature. However, since it is reported that there are over 7600 worldwide species of ants, which comprise at least nine subfamilies within the family formicidae, most ant venoms have not been characterized or isolated. The ant venoms which have been characterized have typically been partially characterized or purified. Indeed, the fact that ants typically possess less than 10 μg of venom per individual has posed a practical problem for obtaining ant venom in reasonable quantity and purity for biochemical or clinical studies and therefore has been partially responsible for the lack of information concerning ant venoms.

A wide variety of proteins, peptides and fairly volatile organic compounds have been reported as being present in ant venom. The proportions of these components is known to vary between species of ants. For instance, the venom of fire ants (*Solenopsis invicta* and *S. richteri*) consists predominantly of piperidine alkaloids. The *S. invicta* fire ant (the red fire ant) contains a much higher percentage of a particular type of alkaloid then do the native North American fire ants. Fire ant venom also contains small quantities of proteins. In contrast, it is reported that the african Solenopsis, *S. pinctaticipes* venom incorporates an alkaloid composition completely different from those found in the new world fire ants. The sting produced by the venom of this species of ant has a much milder effect on a human than that of the red fire ant.

It is also reported that other ant venoms contain nitrogenous compounds. Other species of ants have been reported to include turpines in their venoms. In addition there is reported to be a wide variety of venoms the bulk of which is comprised of a variety of uncharacterized proteins. For instance, australian Bull Dog ants, *Myrmecia pyriformis* and *M. gulosa*, are reported to have significant pharmacological activity. The venoms of these ants contain histamine, phospholipase A, and peptide fractions (responsible for smooth muscle stimulating), hemolytic factors and histamine-releasing activities. Other subspecies of Bull Dog ant venom are reported to contain different proteinaceous venom components which result in different biological effects upon a human. The venom of the New World harvester ant, *Pogonomyrmex badius*, has been reported to possess at least four different enzymes: hyaluronidase, phospholipase A, acid phosphatase, and esterase.

In light of the above, it is not surprising that the in vivo activity of these crude ant venoms extract would be quite varied. Clearly, many of the in vivo effects of an ant sting or venom extract application to a human would be negative and would, in many cases, be extremely painful and uncomfortable. Indeed, it has been reported that ant stings are capable of causing anaphylaxis in humans and neurotoxic symptoms in mammals.

Crude preparations of ant venoms have, however, been utilized in attempts to treat human ailments such as rheumatoid arthritis; Schultz, D. R. et al, Clinical Research 26 (1), 1978; Schultz, D. R. et al, the Journal of Immunology, 126, 1994–1998 (1981). In addition, the effect on the complement pathway in human serum by polysaccharides from the venom of the tropical ant Pseudomyrmex have also been studied; Dieminger, L. et al, The Journal of Immunology, 123 (5) 1979. Polysaccharides in Pseudomyrmex ant venom have also been isolated and characterized; Schultz, D. R. et al, Molecular Immunology, 16, 253–264, 1979. It has also been reported that crude preparations of ant venom from Pseudomyrmex species have been utilized and shown to have some effect in treating some symptoms of rheumatoid arthritis; Altman, R. D. et al, Arthritis and Rheumatism, 26, (4 suppl.) page S55, 1983; Altman, R. D. et al, Arthritis and Rheumatism, 27, 3 (1984). However, only limited improvements were shown to be as a result of introduction of these crude preparations in an in vivo study. It was reported that 60% of the venom treated patients demonstrated minimal disease activity at the end of a 6 month follow-up, while 40% of the venom treated patients had minimal or no great benefit. It was also reported that response to the venom was not complete in all parameters and that several measurements of active disease failed to demonstrate significant improvement or reduction i.e., walking time, grip strength, ESR, rheumatoid factor and the consumption of nonsteroidal anti-inflammatory drugs. It was also reported that a Pseudomyrmex crude ant venom filtrate contained a factor which was an active anti-inflammatory agent and which apparently had a molecular weight of 1000 or less. This material was said to be not inflammatory and caused the functional inactivation of C3 in normal human serum in vitro; Byrnes, J. J. et al, Clinical Research, Vol. 33, No.2, 1985. Finally, it has also been reported that a purified polysaccharide from Pseudomyrmex has activity as a anti-rheumatoidal agent. U.S. Pat. No. 4,247,540, issued Jan. 27, 1981.

Auto-Immune Diseases—Rheumatoid Arthritis

Autoimmune diseases may generally be defined as disorders in which the immune system produces autoantibodies to an endogenous antigen(s) resulting in injury to endogenous tissues. A number of different diseases are believed to be the result of an autoimmune disorder. The exact factors which cause or initiate these disorders have not been definitely characterized; however, genetic factors are believed to play an important part. Diseases which are believed to be the result of autoimmune disorders include, for instance, systemic lupus erythematosus, Graves' disease, Myasthemia gravis, mixed connective tissue disease and rheumatoid arthritis.

Autoimmune disorders typically share similar immunologic and inflammatory alterations of connective tissue. Rheumatoid arthritis (hereinafter alternatively referred to as RA), for example, is a chronic systemic inflammatory disease which principally affects the synovial membranes of the peripheral joints. It is characterized by the proliferation of synovial cells and progressive destruction of articular and periarticular structures. Its cause is unknown. Synovial deposition of aggregated IgG-Rheumatoid Factor (RF)-complement complexes occurs in RA. Rheumatoid factor (RF) is typically an IgM globulin (occasionally IgG or IgA) with specificity for a determinant on the constant region of the heavy chain of autologous IgG. The IgG-RF-complement aggregates are also found within neutrophils, wherein they cause the release of lysosomal enzymes which contribute to the inflammatory joint reaction. Plasma cells are also present in large numbers within the joint, and may synthesize anti-IgG antibodies. Thymus derived (T) cells and lymphokines are also found in rheumatoid joints and contribute to the inflammatory joint reaction.

The American Rheumatism Association has established criteria for the diagnosis of "possible," probable," "definite," and "classic" RA (see Bulletin on Rheumatic Diseases, Vol. 9, No. 4, pp.175-176, December 1958, and Primer on the Rheumatic Diseases. JAMA, Vol. 224, p. 799, Apr. 30, 1973; American Medical Association.) While primarily intended as a communication aid for those in clinical research, these criteria can serve as a guide to clinical diagnosis of RA. For Example some of the following criteria may be utilized:

1. Morning stiffness.
2. Pain on motion or tenderness in at least 1 joint.
3. Swelling (soft tissue thickening or fluid, not bony overgrowth alone) in at least 1 joint (observed by a physician).
4. Swelling (observed by a physician) of at least 1 other joint (any interval free of joint symptoms between the 2 joint involvements may not be more than 3 mo).
5. Symmetric joint swelling (observed by a physician) with simultaneous involvement of the same joint on sides of the body.
6. Subcutaneous nodules (observed by a physician) over bony prominences, on extensor surfaces, or in juxta-articular regions.
7. X-ray changes typical of rheumatoid arthritis.
8. Positive agglutination test—demonstration of the rheumatoid factor by any method which, in 2 laboratories, has been positive in not <5% of normal controls.
9. Poor mucin precipitate from synovial fluid (with shreds and cloudy solution).
10. Characteristic histologic changes in synovial membrane
11. Characteristic histologic changes in nodules showing granulomatous foci with central zones of cell necrosis, surrounded by a palisade of proliferated mononuclear cells, peripheral fibroses, and chronic inflammatory cell infiltration.

Methods of Treatment of Rheumatoid Arthritis

Even though the underlying cause of RA is unknown, various treatments have been utilized in order to alleviate the symptoms, i.e. pain, inflammation and swelling, that accompany this disease. Conservative treatment methods include rest, application of heat and cold and, when appropriate, physical therapy and exercise.

Additional means of treatment include providing the affected individual with non-steroidal anti-inflammatory drugs including aspirin (salicylates), ibuprofen, (Motrin®), Indomethacin, fenoprofen (Nalfon®), naproxen (Naprosyn®), tolmetin (Tolectin®), sulindac (Clinorn®), meclofenamate sodium (Meclomen®), and piroxicam (Feldene®). However, many of these drugs can result in serious gastrointestinal and other problems.

Another anti-inflammatory drug utilized in RA treatment includes the antimalarial, Hydroxychloroquine sulfate (Plaquenil®). However, this drug can lead to serious visual, skeletal and muscle problems. Gold salts have been used in treatment of RA. There is evidence that these agents may retard the bone erosions of rheumatoid arthritis. Indeed, a high number of patients benefit from gold therapy. However, toxic reactions to gold salts are common. Penicillamine has also been used in patients suffering from severe RA although its toxicity is substantial.

Corticosteroids have been utilized for their anti-inflammatory effect in the treatment of RA although serious problems may develope through their long-term use.

In sum, most of the approved drugs utilized to treat RA can have serious side effects and are typically effective only during the course of treatment. Except for gold salts, most of the above compounds evidence little or no ability to relieve RA symptoms suffered by a patient once they are withdrawn.

It is, therefore, an object of the present invention to provide a safe and long lasting agent for the treatment of RA and its related symptoms.

It is also an object of this invention to provide a highly purified, non-polysaccharide, anti-inflammatory, immunosuppressive and analgesic compound which has highly enhanced activity in the treatment of autoimmune diseases such as RA than that of crude preparations while maintaining low levels of adverse effects upon in vivo administration.

It is a further object of this invention to provide a method for the preparation of a highly purified anti-inflammatory, immunosuppressive and analgesic compound. It is another object of this invention to provide a pharmaceutical composition which includes the anti-inflammatory, immunosuppressive and analgesic compound.

It is an additional object of this invention to provide a method for treatment of auto-immune diseases with the highly purified and active compound or related pharmaceutical composition which provides for long lasting results and no adverse side affects.

SUMMARY OF THE INVENTION

Generally stated, the invention as disclosed and described herein includes an anti-inflammatory and analgesic compound which may be derived from ant venom, a method of producing the anti-inflammatory and analgesic compound, a pharmaceutical composition which incorporates the anti-inflammatory and analgesic compound and a method of treating an auto-immune disease with this compound. An ant venom extract particularly useful with this invention is obtained from an ant of the genus Pseudomyrmex, and preferably *Pseudomyrmex triplarinus*. The venom present in this ant is located in and extracted from its venom sac. The anti-inflammatory and analgesic compound derived from this ant venom has an infrared absorption spectrum having absorption at about 3120 cm$^{-1}$, 3020 cm$^{-1}$, 1480 cm$^{-1}$, 1400 cm$^{-1}$ and 950 cm$^{-1}$ with no characteristic absorption at about 1640 cm$^{-1}$ and 1540 cm$^{-1}$.

This invention also includes a pharmaceutical composition for treatment of autoimmune diseases comprising the anti-inflammatory and analgesic compound having an infrared absorption spectrum having characteristic absorption at about 3120 cm$^{-1}$, 3020 cm$^{-1}$, 1480 cm$^{-1}$, 1400 cm$^{-1}$ and 950 cm$^{-1}$ with no characteristic absorption at about 1640 cm$^{-1}$ and 1540 cm$^{-1}$ and a pharmaceutically acceptable carrier material.

In addition, this invention also provides a method of treating an individual effected with an auto-immune disease comprising providing to said individual an effective amount of the pharmaceutical composition comprising an anti-inflammatory and analgesic compound having an infrared absorption spectrum having characteristic absorption at about 3120 cm$^{-1}$, 3020 cm$^{-1}$, 1660 cm$^{-1}$, 1480 cm$^{-1}$, 1400 cm$^{-1}$ and 950 cm$^{-1}$ with no characteristic absorption at about 1640 cm$^{-1}$ and 1540 cm$^{-1}$ and a pharmaceutically acceptable carrier material.

One such auto-immune disease treatable by this method is rheumatoid arthritis. This method has been shown to reduce swelling and inflammation and relieve pain caused by an auto-immune disease in an individual suffering from an auto-immune disease. It has been found that treatment according to this method relieves pain and reduces swelling for at least about 4 weeks after a treatment regime of about 0.5 ml to about 1.0 ml per day of the pharmaceutical composition when given to the suffering individual for a period of about 10 days. Indeed, the treatment appears to cause remission of rheumatoid arthritis conditions for an as yet undetermined period of time which period of time may be months, years or for the duration of the patients life.

This invention further provides three alternative methods for producing the anti-inflammatory and analgesic compound characterized by an infrared absorption spectrum having characteristic absorption at about 3120 cm$^{-1}$, 3020 cm$^{-1}$, 1660 cm$^{-1}$, 1480 cm$^{-1}$, 1400 cm$^{-1}$ and 950 cm$^{-1}$ with no characteristic absorption at about 1640 cm$^{-1}$ and 1540 cm$^{-1}$.

Essentially, the first method comprises:
1) collecting liquid venom from *Pseudomyrmex triplarinus* ants;
2) diluting said liquid venom with an aqueous solution;
3) removing the contaminants in the aqueous venom solution;
4) providing said venoms extract to a hydrophilic vinyl resin adsorption chromatographic column and eluting said venom extract solution with a salt solution;
5) providing said aqueous venom solution to cation exchange chromatographic column and eluting said aqueous venom solution with a salt solution said resulting venom extract being said anti-inflammatory and analgesic compound.

The second alternative method comprises:
1) collecting liquid venom from *Pseudomyrmex triplarinus* ants;
2) diluting said liquid venom with an aqueous solution;
3) removing contaminants from said aqueous venom solution;
4) heating said aqueous venom solution of step 3 to at least about 90° C. for about 5 minutes;
5) cooling said heated aqueous venom solution to about 20° C.;
6) filtering said cooled aqueous venom solution to remove water insoluble components;
7) providing said aqueous venom solution to a hydrophilic vinyl resin adsorption chromatographic column and eluting said venom extract solution with a salt solution;
8) providing said aqueous venom solution to cation exchange chromatographic column and eluting said aqueous venom solution with a salt solution said resulting venom extract being said anti-inflammatory and analgesic compound.

The third method comprises:
1) collecting liquid venom from *Pseudomyrmex triplarinus* ants;
2) diluting said liquid venom with an aqueous solution;
3) removing contaminants from said aqueous venom solution;
4) providing said aqueous venom solution of step 3 to an anion exchange resin chromatographic column and eluting said aqueous venom solution with water;
5) providing said aqueous venom solution of step 4 to a hydrophilic vinyl resin adsorption chromatographic column and eluting said venom extract solution with a salt solution; and
6) providing said aqueous venom solution to cation exchange chromatographic column and eluting said aqueous venom solution with a salt solution said resulting venom extract being said anti-inflammatory and analgesic compound.

The anti-inflammatory and analgesic compound set forth above in all of the various aspects of the invention may be further characterized by the following:
(a) a negative stain test for compounds having high contents of glycoprotein, heparin, chondroitin sulfuric acid, polysaccharides and other hydrocarbons with periodic acid Schiff reagent (PAS);
(b) a negative color forming test result with anthrone reagent;
(c) a negative color forming test result for uronic acid by carbazole sulfate method;
(d) a negative absorption test result for a compound having a mannose and glucose residue with Concanavalin A sepharose;
(e) a fractional molecular weight of less than about 1000 daltons; and
(f) an inhibitory activity on normal human serum complement third component.

In the above methods for producing the anti-inflammatory and analgesic compound the hydrophilic vinyl resin used is preferably a cross-linked polyvinyl alcohol. As an example, the ant venom extract is eluted as a single peak at a concentration of about 50 to about 250 mM after about 108 minutes with the elution from this column being carried out with a salt solution flowing at a rate of about 1 ml per centimeter squared.

The salt solution utilized in the final step also contains from about 5 to about 1000 mM salts. The pH of the venom extract at the end of this method is from about 4 to about 8 with the concentration of the venom extract being about 5 to about 1000 mM. The anion exchange resin utilized in this method preferably comprises a water insoluble high molecular weight carbohydrate containing diethyl amino group such as DEAE-cellouse and DEAE-Sepharose.

A more detailed description of the invention is provided below.

DETAILED DESCRIPTION OF THE INVENTION

Figure 1:
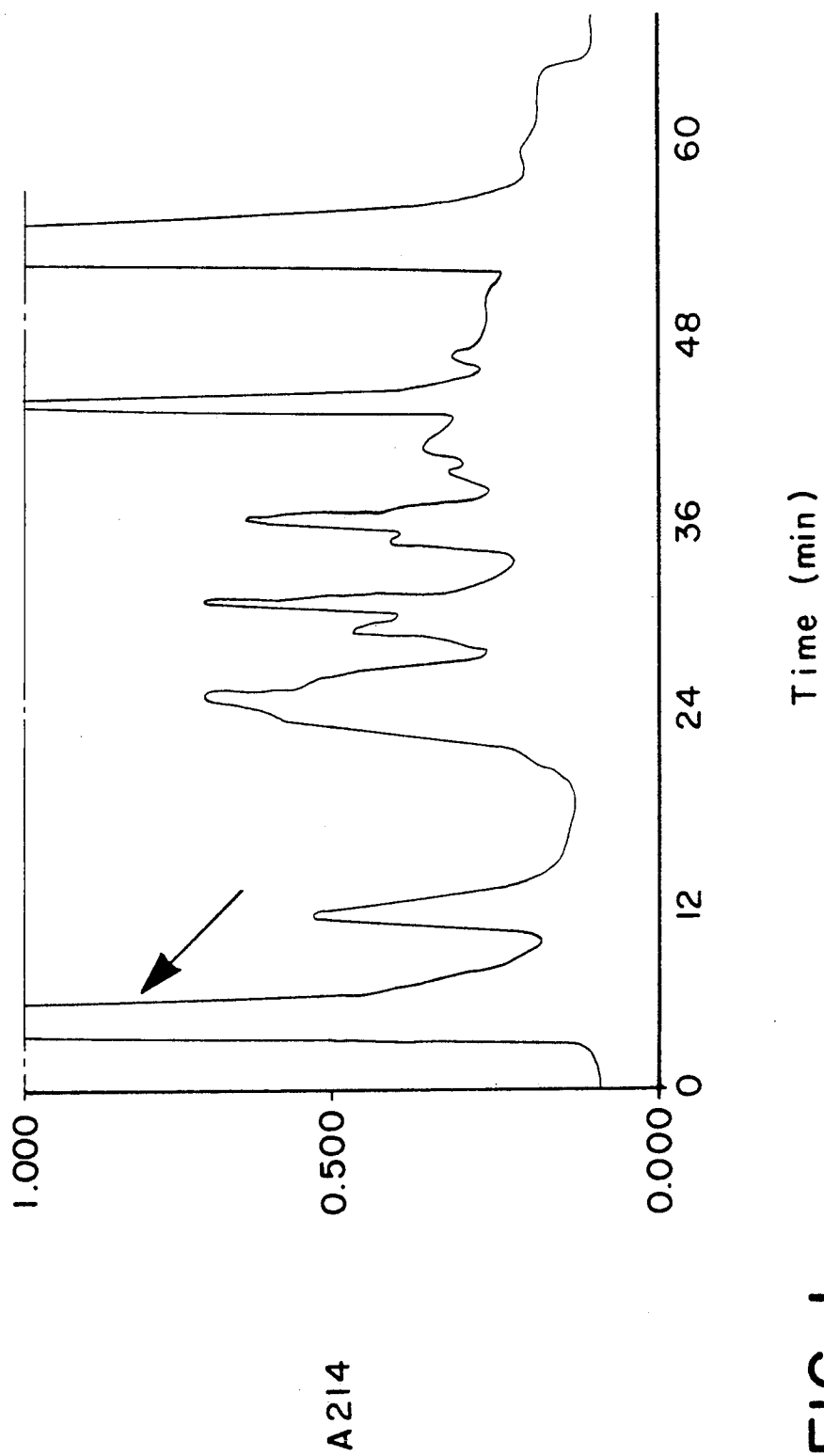
FIG. 1 shows anion exchange chromatography wherein arrow shows the elution peak of the first isolated extraction fraction, EP-1.

This invention discloses and relates to a novel anti-inflammatory, immunosuppressive and analgesic compound having an infrared absorption spectrum having characteristic absorption at about 3120 cm$^{-1}$, 3020 cm$^{-1}$, 1480 cm$^{-1}$, 1400 cm$^{-1}$ and 950 cm$^{-1}$ with no characteristic absorption at about 1640 cm$^{-1}$ and 1540 cm$^{-1}$.

More specifically this compound is further characterized by the following:

(a) a negative stain test for compounds having high contents of glycoprotein, heparin, chondroitin sulfuric acid, polysaccharides and other hydrocarbons with periodic acid Schiff reagent (PAS);

(b) a negative color forming test result with anthrone reagent;

(c) a negative color forming test result for uronic acid by carbazole sulfate method;

(d) a negative adsorption test result for a compound having a mannose and glucose residue with Concanavalin A sepharose;

(e) a fractional molecular weight of less than about 1000 daltons (preferably as determined with an ultrafiltration membrane); and (f) an inhibitory activity on normal human serum complement third component.

Ants of the Genus Pseudomyrmex species triplarinus, which have stingers and venom sacs in their abdomens, are preferably utilized as the production source of the anti-inflammatory and analgesic compound of the present invention. As a preferred method for collecting the venom from such ants, a specially designed box is placed along the trunk or limb of a tree in which Pseudomyrmex triplarinus are known to reside. The box is outfitted on its top surface with a screen which is affixed to the four side walls of the box. Under the screen, separated by a short distance, is a glass plate which is removably attached via a water tight seal to the side walls of the box. Distilled water is placed onto the glass plate so as to cover its surface to a shallow depth. The collector taps on the tree to stimulate an "attack" on the box by the ants. Ants present in the tree then attempt to sting the screen on the box. This results in venom dropping from the ant stingers into the distilled water present beneath the screen. After a suitable period of time, the ants are removed from the box. The aqueous venom solution may then be collected and stored in an appropriate container.

As a slower and more laborious alternative procedure for collecting venom, venom sacs may be gathered by pulling the venom sacs from the abdomens of collected ants using a pincette, together with stingers or stings. The whole venom sacs of the ants are then macerated (a venom fluid is collected from the sacs) and the solid contents are separated by filtration or centrifugation. Alternatively, collected ants are put in a net or an appropriate container. The ants are then subjected to vibration or sound which excites the ants whereby the venom is then secreted from stings in response to the vibration or sound.

A suitable amount of distilled water or physiological saline is then added to these raw materials collected from the ants. After diluting the mixture, the aqueous venom solution may also be passed through a filter (preferably No. 1 gauge) to give an aqueous extract of the venom. More preferably, a pale yellow aqueous extract can be obtained by passing through a ultrafiltration membrane having a fractional molecular weight of 10,000 (for example, Amicon YM10) or a ultrafiltration membrane having a fractional molecular weight of 1,000 (for example, Amicon YM2). If necessary and desired, distilled water is added to adjust to an appropriate concentration.

In many cases, the concentration of the aqueous venom solution is adjusted to an absorbancy of 0.25 to 2.00 at 280 nm and an absorbancy of 2.50 to 20.00 at 214 nm. The method of extracting the venom of ants with water and its concentration are not particularly limited.

According to the present invention, the aqueous venom solution from the venom sac of Pseudomyrmex triplarinus ants is brought into contact with a hydrophilic vinyl resin. In sum, this procedure for producing the anti-inflammatory and analgesic compound of the present invention essentially comprises:

1) collecting liquid venom from Pseudomyrmex triplarinus ants;

2) diluting said liquid venom with an aqueous solution;

3) removing the contaminants in the aqueous venom solution;

4) providing said venom extract to a hydrophilic vinyl resin adsorption chromatographic column and eluting said venom extract solution with a salt solution; and 5) providing said aqueous venom solution to cation exchange chromatographic column and eluting said aqueous venom solution with a salt solution said resulting venom extract being said anti-inflammatory and analgesic compound.

Prior to contact with the hydrophilic vinyl resin column, however, contaminants in the aqueous venom solution can preferably be removed by the following methods as set forth below:

(1) After a heat treatment of the aqueous venom solution, insoluble parts formed are removed by filtration. The heat treatment may be conducted by directly boiling the aqueous venom solution; preferably, the aqueous venom solution is charged in an appropriate glass container, the glass container is immersed in boiled water for several minutes and after cooling to room temperature, the water insoluble parts are removed in a conventional manner such as ultrafiltration or centrifugation, etc.

(2) After cooling the aqueous venom solution or freezing and thawing it again, water insoluble parts formed are removed as in (1) above.

(3) The aqueous venom solution may also be brought into contact with anion exchange resins to remove components adsorbed to the resins prior to contact with the hydrophilic vinyl resin column. It is preferred to use water insoluble high molecular weight carbohydrates containing a diethylamino group such as DEAE-cellulose, DEAE-Sepharose, etc. as the anion exchange resins. A method preferred for this purpose is one that non-adsorbed fraction is fractionated by FPLC chromatography (Pharmacia Fine Chemicals) using a commercially available Mono Q column using distilled water as a moving phase.

These procedures may also be described as follows:

I: 1) collecting liquid venom from *Pseudomyrmex triplarinus* ants;
2) diluting said liquid venom with an aqueous solution;
3) removing contaminants from said aqueous venom solution;
4) heating said aqueous venom solution of step 3 to at least about 90° C. for about 5 minutes;
5) cooling said heated aqueous venom solution to about 20° C.;
6) filtering said cooled aqueous venom solution to remove water insoluble components;
7) providing said aqueous venom solution to a hydrophilic vinyl resin adsorption chromatographic column and eluting said venom extract solution with a salt solution;
8) providing said aqueous venom solution to cation exchange chromatographic column and eluting said aqueous venom solution with a salt solution said resulting venom extract being said anti-inflammatory and analgesic compound.

or II:
1) collecting liquid venom from *Pseudomyrmex triplarinus* ants;
2) diluting said liquid venom with an aqueous solution;
3) removing contaminants from said aqueous venom solution;
4) providing said aqueous venom solution of step 3 to an anion exchange resin chromatographic column and eluting said aqueous venom solution with water;
5) providing said aqueous venom solution step 4 to a hydrophilic vinyl resin adsorption chromatographic column and eluting said venom extract solution with a salt solution; and
6) providing said aqueous venom solution to cation exchange chromatographic column and eluting said aqueous venom solution with a salt solution said resulting venom extract being said anti-inflammatory and analgesic compound.

To obtain the pharmaceutical composition of the present invention, preferably from the venom of *Pseudomyrmex triplarinus* ants, an aqueous venom solution is brought into contact with and adsorbed to the hydrophilic vinyl resin and the adsorbed component is eluted with a salt solution.

The hydrophilic vinyl resin preferred to be used in the above method described above, is a cross-linked polyvinyl alcohol, which is commercially available under names of, for example, Toyopearl HW-40, HW-50, HW-55, HW-60 and HW-75 (Toyo Soda Mfg. Co., Ltd.) or Asahipack GS-310, GS-510, GS-220, GS-320, GS-520, GS-620 and GS-710 (Asahi Chemical Industry Co., Ltd.), etc. Particularly preferred are GS-220 and GS-320. The aqueous venom solution described above is applied to a column packed with these hydrophilic vinyl resins and development is eluted with distilled water at about room temperature, 5° C. to about 35° C., whereby the system is fractionated into about 5 to 10 major fractions.

After washing the column with a sufficient amount (once or twice the column volume) of distilled water, the fraction adsorbed to the hydrophilic vinyl resins is immediately eluted with a salt solution preferably containing 5 to 1,000 mM salts, for example, which may be selected from the group consisting of an aqueous solution of sodium chloride, potassium chloride, sodium phosphate, potassium phosphate, sodium carbonate, potassium carbonate, sodium acetate or potassium acetate to collect the fraction. A pH of the eluate is not particularly limited but a pH range of 4.0 to 8.0 is generally preferred. In order to prevent denaturation of the active component contained in the eluted fraction, a pH range of 5.0 to 6.0 is more preferred.

Further, it is generally appropriate that the concentration of the eluted part be 5 to 1,000 mM. When the ionic intensity is too low, the eluted fraction becomes broad and overly diluted. Conversely, when the ionic intensity is too high, the osmotic potential of the solution becomes large so that inconvenient results are given in the preparation of the pharmaceutical composition. It is, therefore, most preferred that the concentration of the eluate be controlled to be about 50 to about 250 mM. As a cation exchanger used in the procedure described above, there is a porous silica or vinyl resin having carboxylate groups or sulfonate acid groups, which is commercially available under names of, for example, Nucleosil 5SA, 10SA, (Nagel & Co.,), Lichrosorb KAT (Merck & Co., Inc.), Partisil 10SCX (Whatman Inc.) Asahipak ES502C. (Asahi Chemical Industries Co., Ltd.), Ultron PAS (Shinwa Kako Co., Ltd.), Shodex Ionpak KS-801, KC811 (Showa Denko), TSK Gel SCX (Toyo Soda Mfg. Co., Ltd.), Shimpak ISC (Shimazu Seisakusho Ltd.), etc. Particularly preferred is Ultron PAS with sodium type sulfonated polystyrene. A column packed with one of these cation exchangers is equilibrated with 50 to 2000 mM salt solution. The aqueous venom extract described above is applied in the column and is eluted with the same salt solution at room temperature, whereby the system is fractionated into about 5 to 10 major fractions. As a salt solution, the same solution as was used in the hydrophilic vinyl resin column, such as sodium chloride, potassium chloride, sodium phosphate, potassium phosphate, sodium carbonate, potassium carbonate, sodium acetate, potassium acetate, etc. is used and each fraction is collected. A pH of the salt solution is not particularly limited but in order to prevent denaturation of the component contained in the eluted faction, a pH range of 5.0 to 6.0 is generally preferred as described above.

METHOD FOR MEASUREMENT

The assays described below were utilized in order to characterize the ant venom extracts isolated by the procedures disclosed herein.

Inhibitory activity against normal human serum complement third component (C3)

In a polyproplylene-made tube is put 20 μl of fresh sera collected from normal 10 volunteers and 80 μl of a sample (venom aqueous extract) followed by incubation at 37° C. for 4 hours while sufficiently shaking. The obtained sera is diluted, in sequence, with 0.1% (W/V) gelatin, 2.5% (W/V) glucose and 2.5 mM Veronal buffer containing 0.15 mM $CaCl_2$ and 1 mM $MgCl_2$, pH 7.3 (referred to herein as GGVB) to prepare a sample diluted to 50 to 12,800 times.

Each of the diluted sera samples thus obtained, 200 μl, is mixed with 100 μl of $1 \times 10^8$/ml hemolytic intermediate, $EACI^{gp}4^{hu}$[which is obtained by reacting EA with an excess of guinea pig serum complement first component ($CI^{gp}$) with an excess of human serum complement fourth component ($C4^{hu}$)], 100 μl of human complement second component (C2) containing 100CH50 units/ml and 100 μl of containing 100CH50 units/ml each of human complement fifth component (C5), sixth component (C6) and seventh component (C7) followed by incubation at 30° C. for 30 minutes. 100 μl of eighth component (C8) and ninth component (C9) containing 100CH50 units/ml each is then added to the mixture followed by incubation at 37° C. for another 30 minutes.

1 ml of GGVB, ice-cooled, is then added to the obtained reaction mixture after which centrifugation is carried out at 3,000 rpm for 10 minutes. The supernatant is taken out to measure its absorbancy.

A degree of hemolysis in each diluted sample is determined using distilled water instead of GGVB, when absorbancy at 415 nm obtained upon hemolysis of the $EACI^{gp}4^{hu}$ hemolytic intermediate is made 100%. A dilution magnification (titer) (CH50 units) of sera showing 50% hemolysis is then determined.

The degree of C3 inhibitory activity by the sample is calculated by the following equation:

$$\text{Inhibitory activity (\%)} = \frac{A - B}{A} \times 100$$

wherein
A is the C3 titer in normal human sera treated with distilled water or 0.25M NaCl at 37° C. for 4 hours
B is the C3 titer in normal human sera treated with the sample at 37° C. for 4 hours.

Inhibitory activity against mouse spleen cell growth

RPMI-1640 medium (manufactured by Nissui Pharmaceutical Co., Ltd.), 100 μl, containing 5% bovine fetal serum in which $2 \times 10^6$/ml of BALB/c strain mouse spleen cells are suspended was mixed with 50 μl of the same medium having dissolved therein 10 μg/ml of Concanavalin A and 50 μl of an ant venom extract sample having a definite concentration. After incubation at 37° C. for 48 hours in air containing 5% $CO_2$, 0.5 μCi/μl of $^3$H-thymidine was dropwise added thereto followed by incubation for further 18 hours under the same conditions. The whole mouse spleen cells were recovered by a cell harvester and an intensity of beta rays was measured with a liquid scintillation counter.

In a control with no added sample, spleen cells activated by Concanavalin A showed an incorporation of about 300,000 dpm $^3$H-thymidine. The growth inhibitory activity was calculated by the following equation:

$$\text{Growth inhibitory activity (\%)} = \frac{A - B}{A} \times 100$$

wherein
A is the incorporation of $^3$H-thymidine in control (dpm)
B is the incorporation of $^3$H-thymidine when added with a sample (dpm)

Color forming test by periodic acid Schiff reagent(PAS)

A glass test tube was charged 0.2 ml of an ant venom extract sample and 0.02 ml of 2% periodic acid aqueous solution followed by thorough mixing. After allowing it to stand at room temperature, 1.0 ml of Schiff reagent was added followed by thorough mixing. After allowing it to stand for another 30 minutes at room temperature, a red purple color formed which was compared to a control which used water.

Color forming test by anthrone method

A mixture of 50 ml of 95% sulfuric acid and 10 ml of distilled water was dissolved 100 mg of anthrone. 3 ml of the thus prepared anthrone reagent were added to a glass test tube together with 0.5 ml of an ant venom extract sample solution The test tube then immersed in boiling water for 10 minutes. After cooling to room temperature, colorimetry was conducted by comparing a bluish green color formed to a control which used water.

Color forming test by carbazole sulfate method 0.5 ml of an ant venom extract sample solution was added to a glass test tube. While ice cooling, 3 ml of concentrated sulfuric acid was added the glass tube was then immersed in boiling water for 20 minutes. After cooling to room temperature, 0.1 ml of 95% ethanol solution of 0.1% carbazole was added to the mixture followed by thorough mixing. After allowing the test tube to stand at room temperature for 2 hours, colorimetry of a reddish purple color formed was conducted using water as a control.

Adsorption test by Concanavalin-linked Sepharose A

Concanavalin-linked Sepharose A (Pharmacia Fine Chemicals) was packed in a column of 10 mm in diameter × 100 mm in length and 50 mM NaCl showing pH of 7.0 was passed there through at 1 ml/min. An ant venom extract sample solution, 1 ml, was injected and eluted fractions were collected while monitoring with $A_{214}$. The inhibitory activity on normal human sera C3 by the sample was measured before and after passing through the Concanavalin A column was measured.

Analysis of infrared absorption spectrum

After freeze drying an ant venom extract sample, the sample was further dried in vacuum at room temperature for an additional 20 hours. An infrared absorption spectrum of the sample was measured by diffusion reflection method, using a Fourier transform type infrared spectrophotometer Model FTS-15C (Digilabo Co., Ltd.).

Characterization of Fraction 26

Comparison of the NMR peaks of fraction 26 to standards of known compounds revealed that the active fraction contained the following components: choline chloride, arginine, putrescine, ethanolamine, ammonium chloride, calcium chloride, magnesium chloride and lysine. Based on the amounts of each component found in several different samples of fraction 26, an "average" synthetic venom was created, with the following concentrations in 0.25 NaCl.

| | |
|---|---|
| choline chloride | 2890 μg/ml |
| L-arginine HCl | 1398 μg/ml |
| putrescine HCl | 880 μg/ml |
| ethanolamine | 608 μg/ml |
| ammonium chloride | 1722 μg/ml |
| calcium chloride | 122 μg/ml |
| magnesium chloride | 168 μg/ml |
| L-lysine: 2 HCl | 10 μg/ml |

In clinical studies, the synthetic venom has been shown to be as effective as the natural venom in relieving symptoms of arthritis. These tests and results are shown in detail in Section 5.2.2.

In order to further determine which of the components of the mixture are essential to activity, a series of synthetic mixtures were prepared, each eliminating one of the components. These mixtures were then used in in vitro screenings to determine if the mixture without the specified component was still capable of inhibiting Con A induced lymphocyte proliferation. Inhibition of Con A-induced lymphocyte proliferation is indicative of immunosuppressive and anti-inflammatory activity. A summary of the data is provided in Table 30. Of the eight components of the natural active fraction, only five appear to contribute substantially to activity. The two components that appear to have the greatest effect on activity are arginine and ammonium chloride, as evidenced in a substantial decrease in inhibition of lymphocyte proliferation in their absence. Putrescine, ethanolamine and choline chloride also exhibit a significant effect on activity, but the effects of their individual absence does not appear to be as great as either arginine or ammonium chloride. Although calcium chloride and magnesium chloride and lysine each do show some small contribution to the overall activity of the composition, their presence appears to be preferred rather than essential.

EXAMPLES

Example 1—Preparation of Purified Ant Venom Extract

The following examples describe the preparation of the anti-inflammatory and analgesic compound of the present invention from ant venom. Also set forth are its characteristics and activities and examples demonstrating its potent clinical utility against auto-immune disease.

Aqueous Extraction of Ant Venom

Stings and venom sacs were separated from 150 *Pseudomyrmex triplarinus* ants with a pincette. The stings and venom sacs were then macerated after adding 5 ml of distilled water. The macerated mixture was filtered through a No. 3 glass filter and the filtrate was washed with a small amount of water. The filtrate was collected and distilled water was added to make the whole amount 15 ml. Thereafter, filtration was conducted first through an Amicon YM10 (fractional molecular weight of 10,000) and then through an Amicon YM2 (fractional molecular weight of 1,000) to obtain a venom aqueous extract. The obtained aqueous extract was pale yellow and transparent and showed $A_{280\ nm}=0.485$, $A_{260\ nm}=0.649$, $A_{214\ nm}=2.60$ and a pH of 5.7. After freeze drying, the solid content was 0.89 mg/ml. Inhibitory activity against normal human sera C3 showed 64%.

Pretreatment of Ant Venom (AV) Aqueous Extract to Prepare Fraction EP-1

The ant venom aqueous extract, 100 ml, obtained in section 5.1.1 was concentrated to 10 ml over 30 minutes while heating at 45° C. with an evaporator. After water insoluble parts were removed through 0.22 μm GV filter (Millipore Co., Ltd.), the concentrate was frozen and thawed at room temperature. Traces of insoluble parts were removed by filtering through a 0.22 μm GV filter.

The resultant venom aqueous extract, 1 ml, was applied to FPLC liquid chromatography (Pharmacia Fine Chemicals) at room temperature on Mono Q HR10/10 column using distilled water as a mobile phase. While monitoring at A214 nm, elution was conducted with distilled water at a flow rate of 2 ml/min. The non-adsorbed first fraction, EP-1, 12 ml, was collected and pooled to give 120 ml in total. Other fractions were eluted by NaCl having a maximum concentration of 0.25M. The anion exchange FPLC chromatography result is shown in FIG. 1.

The fraction EP-1 obtained, 120 ml, was concentrated to 12.5 ml by freeze drying. The almost colorless transparent fraction EP-1 showed an inhibitory activity of 99% against normal human sera C3 but no C3 inhibitory activity was noted in other fractions. Further, the fraction EP-1 by such a pre-treatment showed an inhibitory activity of 80% against mouse spleen cell growth which was stimulated with Concanavalin A, even of ⅛ dilution. In addition, the fraction EP-1 was positive in PAS staining test, anthrone color forming test and carbazole sulfuric acid color forming test.

Liquid Chromatography Preparation of Fraction 26

Figure 2:
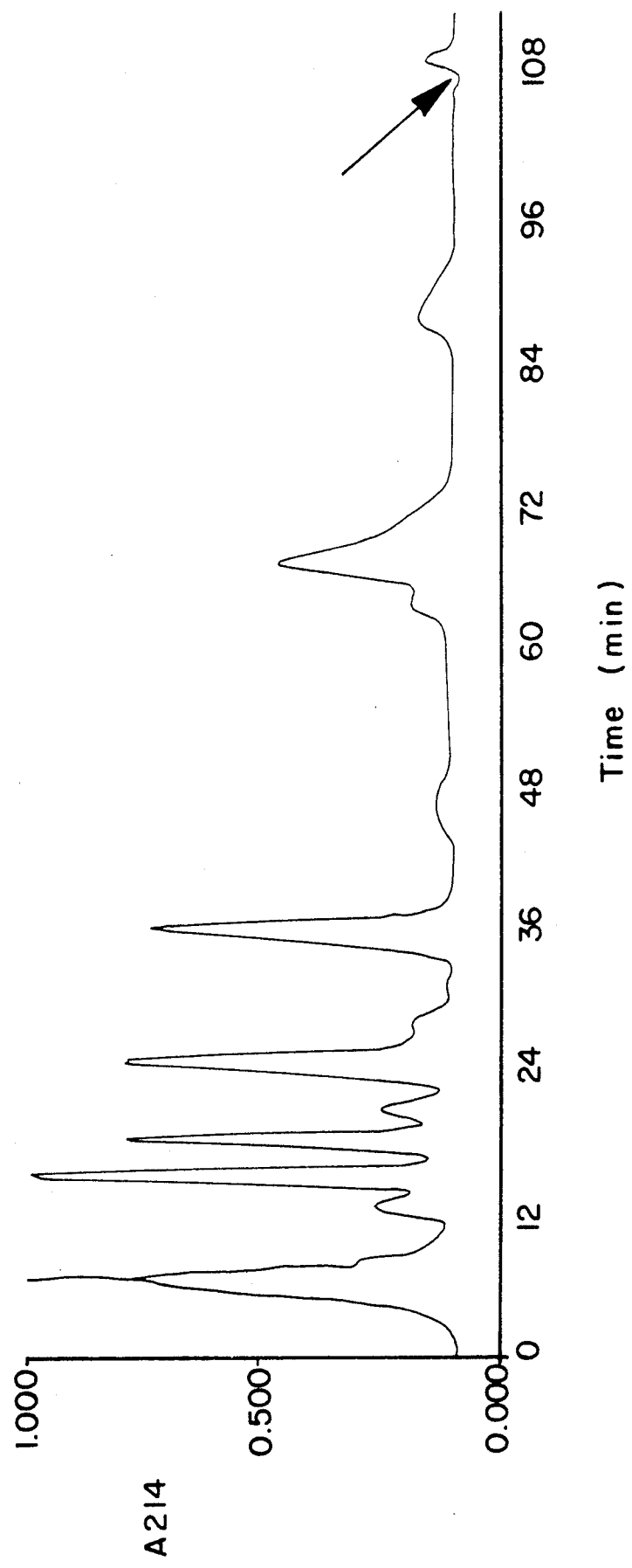
FIG. 2 shows adsorption chromatography wherein arrow shows the elution peak of the ant venom (or equivalently AV) fraction 26.

The fraction EP-1, 4 ml, obtained above was applied to GS320P Column (Asahi Chemical Industry Co., Ltd.) equilibrated with distilled water at room temperature. While monitoring at $A_{214\ nm}$, materials in 5 to 10 main fractions were eluted with distilled water at a flow rate of 1 ml/cm² per minute. Thereafter, a fraction (fraction 26) immediately eluted with 50 mM NaCl showing pH of 4 to 8 was collected and pooled to give 24 ml in total. By freeze drying, the 24 ml sample was concentrated to 4.8 ml. Chromatography of this adsorbed liquid is shown in FIG. 2.

Figure 3:
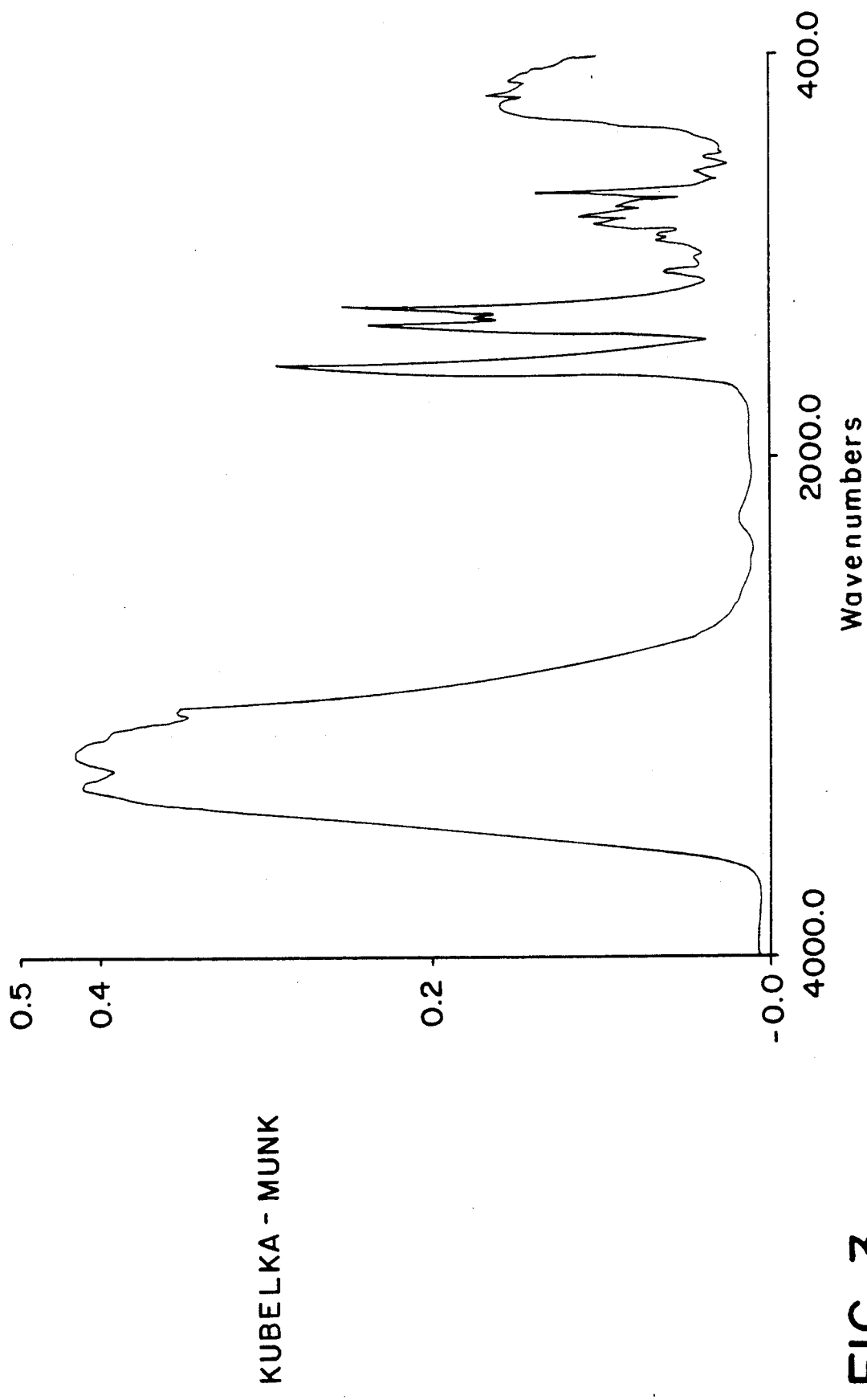
FIG. 3 shows infrared absorption spectrum of the AV fraction 26 fraction (absorption corrected by Kubelka-Munk method; SAMF means Sample No.; RES means Resolution; SCANS means Accumulated Number of Measurements) SAMF=NYS4ABS, RES=8.0 and SCANS=100.

An infrared absorption spectrum of this obtained 26th fraction 26 is shown in FIG. 3. Results obtained in various property tests of the fraction 26 are summarized in Table 1.

TABLE 1

| Item Tested | Results |
|---|---|
| 1 Inhibitory activity against | 93% |

TABLE 1-continued

| Item Tested | Results |
|---|---|
| normal human serum complement third component | |
| 2  Inhibitory activity against mouse spleen cell growth | 60% |
| 3  Color formation of polysaccharides by periodic acid Schiff reagent | negative |
| 4  Color formation of neutral sugars by anthrone reagent | negative |
| 5  Color formation of uronic acid by carbazole sulfate reagent | negative |
| 6  Sugar residue by Concanavalin A-linked Sepharose | negative |
| 7  Infrared absorption spectrum ($cm^{-1}$) | 3120, 3020, 1660, 1480 1400, 950 |

Boiling Test of AV extract

An aqueous venom extract, 10 ml, showing $A_{280\ nm} = 1.65$ and $A_{214\ nm} = 13.3$ and having an inhibitory activity of 33% against normal human sera C3, obtained in a manner similar to section 5.1.1 above, was freeze dried to concentrate to 1 ml. The concentrate was added to a glass test tube, immersed in boiling water for 5 minutes and cooled to room temperature. Thereafter, water insoluble constituents which formed were filtered through Millex GV (Millipore Co., Ltd.) so as to remove them. The venom aqueous extract, 1 ml, was then applied to a Mono Q HR10/10 Column (Pharmacia Fine Chemicals). While monitoring at $A_{214\ nm}$, elution was conducted with 2 ml/min. of distilled water to collect 12 ml of the non-adsorbed first fraction. By freeze drying, the 12 ml first fraction, fraction EP-1, was concentrated to 1.25 ml. This fraction, EP-1, showed an inhibitory activity of 87% against normal human sera C3. From 1 ml of the fraction EP-1 obtained, 2 ml of the fraction 26 was collected in a manner similar to section 5.1.3 above. By freeze drying, 2 ml was concentrated to 0.4 ml. This fraction, designated fraction 26, showed an inhibitory activity of 85% against normal human sera C3.

Boiling Test of Fraction EP-1

A venom aqueous extract, 10 ml, showing $280\ nmA = 1.65$ and $A_{214\ nm} = 13.3$ and having an inhibitory activity of 33% against normal human sera C3, obtained in a manner similar to section 5.1.1 above, was freeze dried to concentrate it to 1 ml. The concentrate was added to a glass test tube, immersed in boiling water for 5 minutes and cooled to room temperature. Thereafter, water insoluble constituents formed were filtered through a Millex GV (Millipore Co., Ltd.) so as to remove them. The venom aqueous extract, 1 ml, was then applied to Mono Q HR10/10 Column (Pharmacia Fine Chemicals). While monitoring at A214 nm, elution was conducted with 2 ml/min. of distilled water to collect 12 ml of the non-adsorbed first fraction (fraction EP-1). By freeze drying, 12 ml of fraction EP-1 was concentrated to 1.25 ml. This fraction, EP-1, showed an inhibitory activity of 96% against normal human sera C3. 1.25 ml of this fraction, EP-1, was added to a glass test tube and immersed in boiling water for 5 minutes. Trace amounts of the water insoluble constituents formed were filtered through a 0.22 μm of Millex GV (Millipore Co., Ltd.) so as to remove them. After treating with boiling water, the fraction EP-1 showed an inhibitory activity of 96% against normal human serum C3, indicating that the C3 inhibitory activity of about 100% was retained.

From 1 ml of the fraction EP-1 obtained by the treatment with boiling water, 2 ml of the fraction 26 was collected in a manner similar to section 5.1.3 above. By freeze drying, 2 ml were concentrated to 0.4 ml. This 26th fraction obtained showed an inhibitory activity of 70% against normal human serum C3.

Inactivation of C3 by Ant Venom Materials

A 200 ml sample of ant venom extract, MW1000, was concentrated to about 18 ml by Savant Speed Vac. (Savant Instrument Inc.) and adjusted to 20 ml with distilled water. After removal of a precipitate by 0.22 μm Millex GV (Millipore Corp.) filtration, this 10 times concentrated material was applied to Mono Q HR10/10 in 2 ml aliquots. A 80 ml of fraction EP-1 was pooled from 10 runs on FPLC, and concentrated to 25 ml.

In the next step, this fraction EP-1 was applied to adsorption FPLC in 4 ml aliquots. The active material was eluted with 50 mM NaCl as fraction 26 (accumulated volume 75 ml). About 98% of the impurities were removed from AV extract MW1000 by the two kinds of FPLC methods (based on peak area at $A_{214}$) A 75 ml of fraction 26 were concentrated to 15 ml and filtration through 0.22 μm Millex GV for sterilization. The AV preparation was aliquoted into sterile vials for evaluating in patients with rheumatoid arthritis (4 ml, 3 vials). The inactivation of C3 in normal human serum by these AV fractions is shown in Table 2 and Table 3.

TABLE 2

Inactivation of C3 in normal human serum by AV materials

| No. | AV Fraction | Concentration | CH50 units/mL of C3 in normal human serum | % Inactivation |
|---|---|---|---|---|
| 1 | distilled water | | 4000 | 0 |
| 2 | 0.25M NaCl | | 4000 | 0 |
| 3 | extract | × 1 | 2080 | 48 |
| 4 | filtrate | × 10 | 4000 | 0 |
| 5 | fraction EP-1[a] | × 2.5 | 40 | 99 |
| 6 | fraction EP-1[a] | × 8.0 | 40 | 99 |
| 7 | fraction 26[b] | × 2.7 | — | — |
| 8 | fraction 26[c] | × 13.3 | 40 | 99 |

Note:
[a] dissolved in distilled water
[b] dissolved in 0.05M NaCl
[c] dissolved in 0.25M NaCl

TABLE 3

Inactivation of C3 in normal human serum by AV fraction 26

| No. | AV fraction | Conc. of NaCl | CH50 units/ml of C3 in normal human serum | % inactivation |
|---|---|---|---|---|
| 1 | | 250 mM | 4000 | 0% |
| 2 | diluted to ¼ | 250 mM | 2200 | 45% |
| 3 | diluted to ½ | 250 mM | 480 | 88% |
| 4 | undiluted | 250 mM | 40 | 99% |

Liquid Chromatographic Preparation of Fraction 41

Fraction 26 obtained as above was condensed into one tenth in volume and 0.5 ml of it was applied to PAS column equilibrated with 1000 nM sodium chloride aqueous solution of pH 5.6 at room temperature. While monitoring with refraction index, Shodex RI SE-61

Figure 4:
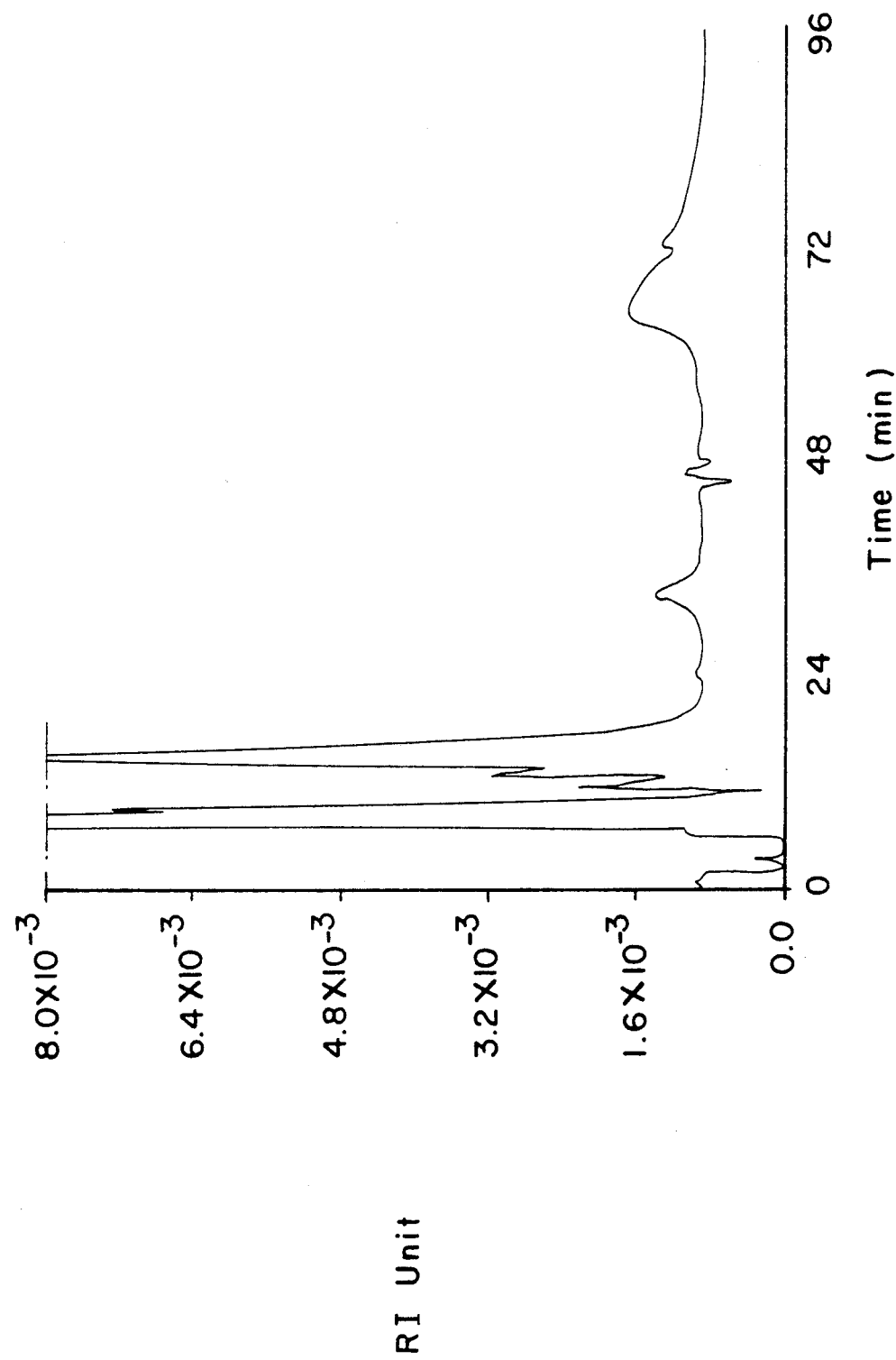
FIG. 4 shows an FPLC chromatogram of AV fraction 26 on a cation exchanges column, PAS.
Figure 5:
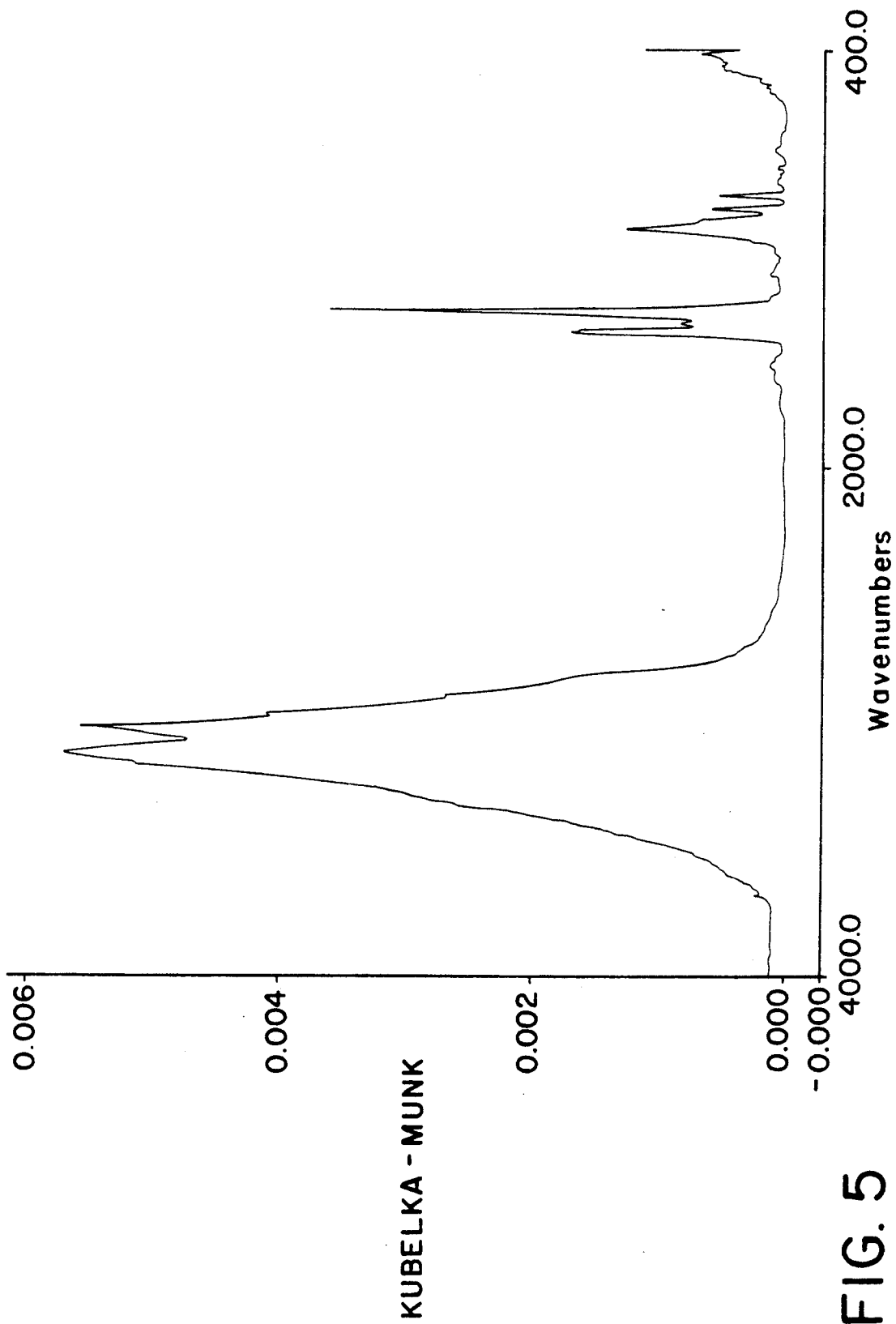
FIG. 5 shows an infrared absorption spectrum of fraction 41 (absorption corrected by Kubelka-Munk method).

(Showa Denko K. K.), a fraction (fraction 41) eluted from the column at a flow rate of 2.4 ml/cm.min, was collected and pooled to give 1.6 ml in total. FIG. 4 shows cation exchange liquid chromatography. FIG. 5 shows an infrared absorption spectrum of the obtained fraction 41. Table 4 shows an inactivation of C3 in normal human serum by the fraction 41. Table 5 summarized results of various property tests of the fraction 41.

TABLE 4

Inactivation of C3 in normal human serum by AV fraction 41

| No. | AV fraction | Conc. of NaCl | CH50 units/ml of C3 in normal human serum | % inactivation |
|---|---|---|---|---|
| 1 | control | 250 mM | 4000 | 0% |
| 2 | diluted to ½ | 250 mM | 1600 | 60% |
| 3 | diluted to ½ | 500 mM | 160 | 96% |
| 4 | undiluted | 1000 mM | 40 | 99% |

TABLE 5

| Item Tested | Results |
|---|---|
| 1 Inhibitory action against normal human serum complement third component | 99% |
| 2 Inhibitory activity against mouse spleen cell growth | N/D |
| 3 Color formation of polysaccharides by periodic acid Schiff reagent | negative |
| 4 Color formation of neutral sugars by anthrone reagent | negative |
| 5 Color formation uronic acid by carbazole sulfate reagent | negative |
| 6 Sugar residue by Concanavalin A-linked Sepharose | negative |
| 7 Infrared absorption spectrum ($cm^{-1}$) | 3120, 3020 1480, 1400 950 |

Example 2—Clinical Assays

Purified Extract

The following clinical data provides support for the use of ant venom extract fractions 26 and 41, obtained utilizing the procedures as set forth above, for the treatment of patients with auto-immune diseases such as rheumatoid arthritis. The clinical data obtained with fractions 26 and 41 is compared below to the clinical data obtained with fraction 1, designated EP-1. The results below demonstrate signs of improvement in patient symptoms after using fraction 26 or 41 as opposed to EP-1. The following treatment protocol was followed in order to generate the clinical data provided in below and as is summarized in Tables 6-20.

| | TREATMENT PROTOCOL |
|---|---|
| Item | Description |
| 1. Treatment regimes | Minimum of 10 days per patient. |
| 2. Dosages | One-half to 1.0 ml per day for 10 days (depending on the quantity of fraction 26 or fraction 41 available). Albumim added, where indicated, as a stabilizer. |
| 3. Schedule | Injection every day except week-ends. Total of 10 days of injections. |
| 4. Mode of administration | Subcutaneous, upper extremities. |
| 5. Comments interpreting the numerical data set forth in the tables. | Interpretations are based on criteria accepted by the F.D.A. and the American Rheumatism Association. Altman et al, Arthritis & Rheumatism 1984 (which reference is hereby incorporated by reference). |

In Tables 6-20 the letters for each number (e.g., #82, J. A.) are the patient's initials. The term EP-1 indicates effluent peak no. 1 from Mono Q column (anionic exchanger) in the FPLC System. The term "HA" means headache. The term "NSAID" means Non-steroidal anti-inflammatory drug (e.g , aspirin). In order to establish the Pain Index two criteria were evaluated:

a. The total number of painful joints was determined and
b. The degree of severity for each joint was determined with: 1=mild; 2=moderate; 3=severe. The degree of severity was multiplied ×1=observation for a single joint. Sum the degrees of severity for all joints.

Pain Index =

$$\frac{\text{Total No. of Painful Joints}}{\text{Summation Of Degrees Of Severity For All Joints}}$$

The "Swelling Index" was determined by the same method as the Pain Index. The term "sed rate" means the sedimentation rate of red cells. The term "grip strength" is the average of 3 measurements for each hand. "walking" is a 50-foot walking time in seconds. The term "y.o." means "years old".

The term "Baseline" indicates the patient's condition prior to any treatment with Fraction 26 or 41 or EP-1 and is the time period in which the first clinical impressions are made. Visit #1 one indicates the observed condition of the patient one week after the first injection of the ten day treatment regime. Each following visit, in sequence, took place one additional week after the next injection unless otherwise indicated (e.g., visit #2 came two weeks after the second injection; visit #3 came three weeks after the third injection and so on).

The measurements for each patient with rheumatoid arthritis were taken from the Lansbury criteria as cited in the Am. J. Med. Sci., 232:300-310, 1956 and Arthritis Rheum., 1:505-522, 1958.

TABLE 6

| PT # | LOT # | VISITS | Baseline | 1 Wk | 2 Wk |
|---|---|---|---|---|---|
| Fraction 26 without albumin #90 (B.H.) Female; White 55 years old | INDEX | PAIN | 40/67 | 16/22 | 7/10 |
| | | SWELLING | 33/43 | 14/15 | 5/5 |
| | | SED RATE | 60 | 42 | 41 |
| | | WALKING | 11 | 10 | 13 |
| | | GRIP R | 84 | 106 | 110 |
| | | GRIP L | 60 | 83 | 50 |
| | | | | 3 Wk | 4 Wk |

TABLE 6-continued

| PT # | LOT # | VISITS | | Baseline | | |
|------|-------|--------|---|----------|---|---|
| patient #90, cont. | | INDEX | PAIN | 40/67 | 4/6 | 5/7 |
| | | | SWELLING | 33/43 | 6/7 | 4/4 |
| patient #90, cont. | | SED RATE | | 60 | 47 | 83 |
| | | WALKING | | 11 | 12 | 11 |
| | | GRIP R | | 84 | 96 | 100 |
| | | GRIP L | | 60 | 50 | 80 |

In patient #90 all parameters improved. There was a greater than fifty percent reduction in pain at two weeks and a two-thirds or approximately 66% reduction in swelling. At four weeks, another fifty percent reduction was noted in both pain and swelling. A sore throat lasting twenty-four hours was reported at visit two. At visit four a 2 day headache and pruritus of the trunk were reported.

Patient responded dramatically within the first week of injections. One week following the injections (week 3), there was some increase in pain with continued reduction in swelling. At five weeks there was an increased in pain with a slight increase in swelling. At week eight parameters improved. Pain at injection sites was reported. Walking times improved and a reduction in erythrocyte sedimentation rate was demonstrated.

TABLE 8

| PT # | LOT # | VISITS | | Baseline | 1 Wk | 2 Wk | 3 Wk | 4 Wk | 5 Wk |
|------|-------|--------|---|----------|------|------|------|------|------|
| Fraction 26 without albumin patient #89 (D.H.) | | | | | | | | | |
| Female; White 49 years old Fraction 26 without albumin | | INDEX | PAIN | 30/38 | 32/37 | 10/13 | 11/13 | 12/13 | 23/42 |
| | | | SWELLING | 27/28 | 26/27 | 14/15 | 11/12 | 14/15 | 15/19 |
| | | SED RATE | | 60 | 70 | 70 | 64 | 62 | 80 |
| | | WALKING | | 11 | 13 | 12 | 14 | 15 | Refused |
| | | GRIP R | | N/D | 43 | 50 | 60 | 50 | 40 |
| | | GRIP L | | N/D | 33 | 53 | 43 | 53 | 53 |

All parameters have improved. At week two there was a two-thirds reduction in both painful and swollen joints. The response continued until week four which was the most recent evaluation. Fever, sore throat and hoarseness were reported at visit three; this continued for twelve days. Purulent pharyngitis was present. This responded to antibiotics.

TABLE 9

| PT # | LOT # | VISITS | | Baseline | 1 Wk | 2 Wk | 3 Wk | 4 Wk | 5 Wk | 6 Wk | 8 Wk |
|------|-------|--------|---|----------|------|------|------|------|------|------|------|
| Fraction 26 with 2.5% human albumin patient #86 (B.R.) | | | | | | | | | | | |
| Female; White 70 years old | | INDEX | PAIN | 18/32 | 2/5 | 7/9 | 10/16 | 1/1 | 2/3 | 3/5 | 13/25 |
| | | | SWELLING | 23/25 | 4/5 | 2/2 | 5/14 | 1/1 | 2/2 | 8/8 | 13/13 |
| | | SED RATE | | 25 | 26 | 35 | 30 | 22 | 10 | N/D | 17 |
| | | WALKING | | 21 | 17 | 19 | 25 | 20 | 21 | 21 | 20 |
| | | GRIP R | | 50 | 30 | 36 | 40 | 50 | 60 | 40 | 50 |
| | | GRIP L | | 56 | 54 | 50 | 70 | 70 | 70 | 50 | 60 |

Patient responded dramatically at the first week (day 6) and was in near remission by the second week. One week after discontinuing the injections (week 4), there was increase in the number of painful and swollen joints but still to about half the pretreatment number. Patient continued at same level until week eight when an increase in amount of pain was recorded. Swelling re-

TABLE 7

| PT # | LOT # | VISITS | | Baseline | 1 Wk | 2 Wk | 3 Wk | 4 Wk | 5 Wk | 6 Wk | 8 Wk | 10 Wk |
|------|-------|--------|---|----------|------|------|------|------|------|------|------|-------|
| Fraction 26 with 2.5% human albumin patient #87 (N.T.) | | INDEX | PAIN | 22/54 | 3/8 | 10/10 | 10/15 | 9/17 | 16/48 | 13/26 | 8/21 | 3/3 |
| | | | SWELLING | 38/50 | 5/5 | 6/6 | 4/4 | 4/4 | 19/19 | 13/13 | 5/5 | 3/3 |
| Fraction 26 with 2.5% human albumin | | SED RATE | | 75 | 56 | 39 | 39 | 45 | 50 | N/D | 50 | |
| Female: White 28 years old | | WALKING | | 17 | 11 | 13 | 13 | 11 | 11 | 13 | 12 | 11 |
| | | GRIP R | | 46 | 50 | 50 | 56 | 50 | 36 | 50 | 43 | 44 |
| | | GRIP L | | 40 | 60 | 60 | 66 | 40 | 60 | 50 | 50 | 50 | mained at fifty percent less than baseline. Local reaction was pain at the injection site.

TABLE 10

| PT # | LOT # | | VISITS | Baseline | 1 Wk | 2 Wk | 3 Wk | 4 Wk | 5 Wk | 6 Wk | 8 Wk | 10 Wk |
|---|---|---|---|---|---|---|---|---|---|---|---|---|
| patient #84 (A.B.) | Fraction Ep-1 | | | | | | | | | | | |
| Female; | | INDEX | PAIN | 18/26 | 23/28 | 16/38 | 45/111 | 22/39 | 9/17 | 13/26 | | 28/67 |
| White | | | SWELLING | 19/23 | 17/18 | 17/17 | 18/23 | 23/26 | 11/11 | 14/15 | | 23/34 |
| 54 years old | | | SED RATE | 48 | 44 | 59 | N/D | 55 | N/D | 55 | | |
| | | | WALKING | 28 | 28 | 30 | 29 | 19 | 20 | 20 | | 30 |
| | | | GRIP R | 80 | 103 | 84 | 63 | 66 | 80 | 80 | | 53 |
| | | | GRIP L | 116 | 123 | 90 | 86 | 60 | 110 | 70 | | 83 |

Joint swelling has showed minimal to moderate improvement with only a slight improvement in pain parameters. The patient was dropped at 10 weeks for lack of efficacy. Local reaction to the injections occurred at injections 12-14.

TABLE 11

| PT # | LOT # | | VISITS | Baseline | 1 Wk | 2 Wk | 3 Wk | 4 Wk | 5 Wk | 6 Wk | 8 Wk | 10 Wk |
|---|---|---|---|---|---|---|---|---|---|---|---|---|
| patient #82 (J.A.) | Fraction Ep-1 | | | | | | | | | | | |
| Female; | | INDEX | PAIN | 36/46 | 8/14 | 6/10 | 5/5 | 6/8 | 4/5 | 12/16 | 6/6 | 14/26 |
| White | | | SWELLING | 19/27 | 10/14 | 4/4 | 1/1 | 1/1 | 2/2 | 4/5 | 2/2 | 6/8 |
| 49 years old | | | SED RATE | 3 | 10 | 10 | 1 | 24 | 12 | 18 | N/D | 28 |
| | | | WALKING | 30 | 17 | 18 | 17 | 35 | 34 | 33 | Refused | Refused |
| | | | GRIP R | 43 | 33 | 53 | 53 | 50 | N/D | 40 | 63 | 50 |
| | | | GRIP L | 23 | 43 | 55 | 66 | 43 | N/D | 45 | 56 | 30 |

All parameters improved. There was a marked reduction in pain and swelling at week one. The effects remained until week twelve. The patient was dropped from study at week twelve due to increasing pain. Flu like symptoms were reported on the day of the last injection lasting only two days.

TABLE 12

| PT # | LOT # | | VISITS | Baseline | 1 Wk | 2 Wk | 3 Wk | 4 Wk | 5 Wk | 6 Wk |
|---|---|---|---|---|---|---|---|---|---|---|
| patient #83 (C.V.) | Fraction Ep-1 | | | | | | | | | |
| Female; | | INDEX | PAIN | 32/84 | 32/74 | 7/8 | 38/68 | 32/62 | 22/27 | 56/139 |
| White | | | SWELLING | 27/35 | 17/17 | 11/11 | 17/17 | 24/26 | 7/7 | 54/89 |
| 49 years old | | | SED RATE | 10 | 34 | 40 | 13 | 18 | 28 | 27 |
| | | | WALKING | 16 | 18 | 17 | 13 | 13 | 11 | 30 |
| | | | GRIP R | 50 | 56 | 43 | 65 | 53 | 70 | Dropped |
| | | | GRIP L | 40 | 40 | 40 | 53 | 43 | 50 | |

There was a moderate improvement in joint swelling and pain at the end of two weeks. Parameters worsened at the six week visit and the patient was dropped from study due to lack of efficacy. Flu like symptoms were reported at one week which were self limiting in 2-3 days.

TABLE 13

| PT # | LOT # | | VISITS | Baseline | 1 Wk | 2 Wk | 3 Wk | 4 Wk |
|---|---|---|---|---|---|---|---|---|
| patient #85 (C.V.) | Fraction EP-1 | | | | | | | |
| Female; | | INDEX | PAIN | 52/132 | 51/129 | 38/82 | 42/113 | DROPPED |
| White | | | SWELLING | 50/78 | 45/65 | 36/38 | 33/42 | |
| 49 years old | | | SED RATE | 30 | 3 | 30 | 26 | |
| | | | WALKING | 14 | 15 | 11 | 13 | |
| | | | GRIP R | 30 | 38 | 25 | 40 | |
| | | | GRIP L | 20 | 30 | 36 | 30 | |

There was minimal improvement in pain parameters with moderate improvement in swelling. Minimal improvement did not persist and the patient discontinued the study at three weeks for lack of efficacy. Pruritus of lips lasting one day only was reported. Also upper respiratory symptoms and headache were noted after one week subsiding in four days. This patient is the same as Patient #83. Patient requested rechallenge with a different fraction.

TABLE 14

| PT # | LOT # | VISITS | | Baseline | 1 Wk | 2 Wk | 3 Wk | 4 Wk | 5 Wk | 6 Wk | 8 Wk |
|---|---|---|---|---|---|---|---|---|---|---|---|
| patient #88 (L.D.) | Fraction EP-1 | | | | | | | | | | |
| Male | | INDEX | PAIN | 50/81 | 41/95 | 26/71 | 54/115 | 38/62 | 47/77 | 38/72 | 47/68 |
| Black 43 | | | SWELLING | 36/43 | 19/21 | 10/14 | 28/29 | 19/22 | 12/12 | 15/16 | 9/10 |
| years old | | | SED RATE | 75 | N/D | N/D | 82 | 60 | 56 | 60 | |
| | | | WALKING | 20 | 20 | 22 | 18 | N/D | 17 | 16 | 18 |
| | | | GRIP R | 40 | 50 | 46 | 60 | N/D | 40 | 73 | |
| | | | GRIP L | 40 | 50 | 50 | 70 | N/D | 54 | 96 | |

Injections were administered every other day. The patient has shown only minimal improvement in pain, but showed improvement in swelling. At week two swelling was reduced by fifty percent. At visit eight there was a further decrease in the number of swollen joints. There was an improvement in grip strength and walking time.

Erythrocyte sedimentation rates gradually decreased from 75 to 60 at visit eight. At visit 2 anorexia, nausea, vomiting and diarrhea were reported which lasted two days. Motrin was restarted at week three due to increased pain without increased swelling.

TABLE 15

| PT # | LOT # | VISITS | | Baseline | 1 Wk | 2 Wk | 3 Wk | 4 Wk | 6 Wk | 8 Wk | 10 Wk | 14 Wk | 18 Wk | 22 Wk |
|---|---|---|---|---|---|---|---|---|---|---|---|---|---|---|
| patient #98 (R.R.) | fraction 26 | | | | | | | | | | | | | |
| Black | | IN-DEX | PAIN | 39/61 | 40/54 | 29/54 | 29/62 | 23/33 | 31/68 | 11/12 | 12/22 | 17/27 | 7/13 | 11/11 |
| Male | | | SWELLING | 37/42 | 37/41 | 27/30 | 32/37 | 20/23 | 33/36 | 6/6 | 6/9 | 10/12 | 7/7 | 16/19 |
| 51 y.o. | | | SED RATE | 55 | 70 | 70 | 86 | — | 45 | — | — | — | 65 | — |
| | | | WALKING | 17 | 21 | WC | WC | 20 | 18 | 14 | 15 | 20 | 13 | 14 |
| | | | GRIP R | 66 | 80 | ND | ND | ND | 70 | 100 | ND | 110 | 110 | 90 |
| | | | GRIP L | 70 | 70 | ND | ND | ND | 70 | 90 | ND | 110 | 90 | 80 |

WC = wheelchair
ND = not done

Patient showed a greater than 50% improvement from baseline to 14 weeks. Patient has continued to show improvement with a greater than 90% reduction in the pain and swelling.

TABLE 16

| PT # | LOT # | VISITS | | Baseline | 1 Wk | 2 Wk | 3 Wk | 4 Wk | 5 Wk |
|---|---|---|---|---|---|---|---|---|---|
| patient #100 (A.L.) | fraction 26 | | | | | | | | |
| White male | | INDEX | PAIN | 37/69 | 17/22 | 25/32 | 22/27 | 32/47 | 10/11 |
| 60 years old | | | SWELLING | 34/43 | 23/26 | 26/34 | 22/23 | 20/26 | 15/19 |
| | | | SED RATE | 43 | — | 46 | 33 | 29 | 50 |
| | | | WALKING | 15 | 14 | 17 | 15 | 16 (cane) | 14 |
| | | | GRIP R | 200 | 210 | 240 | 250 | | 250 |
| | | | GRIP L | 210 | 200 | 260 | 240 | | 260 |

| PT # | LOT # | VISITS | | Baseline | 6 Wk | 8 Wk | 10 Wk | 14 Wk | 18 Wk |
|---|---|---|---|---|---|---|---|---|---|
| patient #100, cont. | | | | | | | | | |
| | | INDEX | PAIN | 37/69 | 13/15 | 8/11 | 15/20 | 5/19 | 6/23 |
| | | | SWELLING | 34/43 | 24/30 | 10/12 | 14/20 | 15/20 | 21/21 |
| | | | SED RATE | 43 | ND | 69 | — | — | 9/11 |
| | | | WALKING | 15 | 13 | 15 | 18 (cane) | 18 | 14 |
| | | | GRIP R | 200 | — | 240 | 265 | 260 | 240 |
| | | | GRIP L | 210 | | 230 | 250 | 250 | 240 |

ND = not done

Patient #100 showed moderate reduction in joint pain and swelling with sustained effect up to 10 weeks. Patient continues to show mild to moderate improvement.

TABLE 17

| PT # | LOT # | VISITS | | Baseline | 1 Wk | 2 Wk | 3 Wk | 4 Wk | 5 Wk | 6 Wk | 8 Wk | 10 Wk | 14 Wk | 18 Wk | 22 Wk |
|---|---|---|---|---|---|---|---|---|---|---|---|---|---|---|---|
| patient #102 (B.H.) White | Fraction 26 | INDEX | PAIN | 22/35 | 13/19 | 8/10 | 9/15 | 6/8 | 8/9 | 8/10 | 8/8 | 6/6 | 5/20 6/6 | 6/21 1/1 | 7/19 2/2 |

TABLE 17-continued

| PT # | LOT # | VISITS | Baseline | 1 Wk | 2 Wk | 3 Wk | 4 Wk | 5 Wk | 6 Wk | 8 Wk | 10 Wk | 14 Wk | 18 Wk | 22 Wk |
|---|---|---|---|---|---|---|---|---|---|---|---|---|---|---|
| Female | | SWELLING | 24/27 | 9/11 | 7/8 | 10/12 | 12/14 | 8/8 | 7/7 | 5/5 | 5/5 | 5/5 | 7/7 | 4/4 |
| 55 | | SED RATE | 88 | 72 | 70 | 75 | 60 | 71 | ND | 100 | — | 63 | — | |
| years | | WALKING | 16 | 15 | 14 | 13 | 14 | 12 | 14 | — | 13 | 13 | 14 | 13 |
| old | | GRIP R | 90 | 98 | 80 | 88 | 95 | | | | | | 100 | 70 |
| | | | | | | | | 100/70 | 100/84 | 90/84 | — | | | |
| | | GRIP L | 70 | 80 | 100 | 70 | 80 | | | | | | 76 | 100 |

ND = not done

Patient #102 responded within 2 weeks with moderate to marked improvement on joint examination and showed a sustained effect at 8 weeks. This is the second course of venom extract after 9 months, with duplication of original results. She continues to show marked improvement after 22 weeks.

TABLE 18

| PT # | LOT # | VISITS | Baseline | 1 Wk | 2 Wk | 3 Wk | 4 Wk | 5 Wk |
|---|---|---|---|---|---|---|---|---|
| patient #97 | fraction 41 | | | | | | | |
| (C.K.) White | INDEX | PAIN | 50/127 | 50/79 | 36/61 | 12/29 | 28/47 | 30/51 |
| | | SWELLING | 33/55 | 47/60 | 26/37 | 11/12 | 21/26 | 23/30 |
| Female | | SED RATE | 95 | 105 | 75 | 70 | 60 | 93 |
| 29 | | WALKING | 30 | 20 | WC | WC | WC | WC |
| years | | GRIP R | 24 | 30 | 40 | 40 | ND | 30 |
| old | | GRIP L | 26 | 40 | 56 | 40 | ND | 40 |

| PT # | LOT # | VISITS | Baseline | 6 Wk | 8 Wk | 10 Wk | 14 Wk | 18 Wk | 22 Wk |
|---|---|---|---|---|---|---|---|---|---|
| patient #97 | fraction 41 | | | | | | | | |
| (C.K.) White | INDEX | PAIN | 50/127 | 25/36 | 19/30 | 25/37 | 24/31 | 17/17 | |
| | | SWELLING | 33/55 | 23/23 | 18/18 | 14/16 | 16/16 | 18/18 | |
| Female | | SED RATE | 95 | ND | 100 | ND | 60 | ND | 42 |
| 29 | | WALKING | 30 | WC | 24 | WC | 18 | 14 | 15 |
| years | | GRIP R | 24 | 50 | 50 | 40 | 60 | 66 | 80 |
| old | | GRIP L | 26 | 50 | 50 | 52 | 34 | 56 | 90 |

WC = wheelchair
ND = not done

Patient #97 had moderate to marked improvement from baseline to week 22. She has continued to show marked improvement in all parameters.

TABLE 19

| PT # | LOT # | VISITS | Baseline | 1 Wk | 2 Wk | 4 Wk | 5 Wk | 6 Wk | 7 Wk | 8 Wk | 10 Wk |
|---|---|---|---|---|---|---|---|---|---|---|---|
| patient #101 | fraction 41 | | | | | | | | | | |
| (R.L.) White | INDEX | PAIN | 43/70 | | | 52/92 | 50/94 | 52/92 | 33/49 | 54/94 | 55/83 |
| | | SWELLING | 32/42 | | | 30/60 | 23/34 | 29/32 | 17/17 | 41/46 | 31/35 |
| Female | | SED RATE | — | — | — | — | 76 | 89 | 60 | 46 | — |
| 36 years | | WALKING | 16 | | | | 17 | 17 | 16 | 20 | 17 |
| old | | GRIP R | | | | | | 80 | | | 100 |
| | | GRIP L | | | | | | 80 | | | 110 |

Patient #101 had slight improvement in joint swelling with continued pain. Patient developed skin rash of unknown origin after 3 injections. Injections of fraction 41 were halted. Patient also halted concurrent antibiotic treatment which was being used to treat unrelated condition. After 2 weeks, skin rash resolved and injections were resumed with recurrence of rash after injection no. 7. Injections were again resumed after 5 days. Rash resolved after completion of injections and no other adverse reactions were observed.

TABLE 20

| PT # | LOT # | VISITS | Baseline | 1 Wk | 2 Wk | 3 Wk | 4 Wk | 5 Wk | 6 Wk | 10 Wk | 14 Wk |
|---|---|---|---|---|---|---|---|---|---|---|---|
| patient #104 | fraction 41 | | | | | | | | | | |
| (B.N.) White; | INDEX | PAIN | 49/105 | 32/39 | 32/66 | 32/66 | 32/47 | 20/21 | 18/28 | 22/40 | 27/37 |
| | | SWELLING | 37/43 | 25/30 | 18/19 | 16/20 | 24/29 | 13/13 | 14/14 | 15/18 | 24/28 |
| Female | | SED RATE | 70 | 80 | 51 | 69 | 108 | 83 | ND | 34 | — |
| 41 years | | WALKING | 18 | 14 | ND | 20 | 18 | 17 | 12 | 16 | 12 |
| old | | GRIP R | 80 | 110 | ND | 110 | 98 | 100 | 150 | 110 | 130 |
| | | GRIP L | 60 | 70 | | 110 | 100 | 100 | 140 | 120 | 120 |

ND = not done

Patient #104 had a slower response to venom extract with moderate to marked reduction in pain and swelling. This began at week 5 and remained at week 6. Improvement in grip strength and reduction in sedimentation rates have not always corresponded with other parameters (joint pain and swelling). This patient continues to improve moderately in pain and swelling compared to baseline.

In sum, the seven patients who were injected with ant venom extract fraction 26 responded positively, and most were dramatically improved. Two of the three patients injected with ant venom extract faction 41 responded positively. It may be concluded, thereby, that the two fractions (26 and 41) contain an active anti-inflammatory and analgesic compound based on the results with the above patients.

Synthetic Venom

To confirm the identity of activity of the synthetic venom with the natural venom, the two were compared in a double-blind study on eight patients conducted by a certified rheumatologist. The synthetic venom used had the composition described above in Section 4.1.8, and was formulated at Toyobo Company, Osaka, Japan. The protocol for administration was as described for testing of the natural venom alone. Four patients (115, 116, 119 and 120) were given synthetic venom and the remaining four natural venom. The treatment history of each patient is outlined in Tables 21-28. Abbreviations and explanations of indices, etc., are as noted above.

TABLE 21

| PT # | LOT # | VISITS | | Baseline | 2 Wk | 3 Wk | 4 Wk | 5 Wk | 6 Wk | 8 Wk | 10 Wk | 14 Wk | 18 Wk | 20 Wk |
|---|---|---|---|---|---|---|---|---|---|---|---|---|---|---|
| patient #114 | Venom Fraction (1-1) | | | | | | | | | | | | | |
| E.R., | INDEX | PAIN | | 11/15 | 17/27 | 12/20 | 10/10 | 12/17 | 9/12 | 11/14 | 4/6 | 14/19 | 8/9 | 5/6 |
| Fe- | | SWELLING | | 22/24 | 18/24 | 9/14 | 7/14 | 8/9 | 5/6 | 18/20 | 11/16 | 9/16 | 9/15 | 5/8 |
| male; | | SED RATE | | 79 | 64 | 27 | 6 | 22 | 21 | ND | 40 | ND | 72 | ND |
| cauc. | | WALKING | | 12 | 14 | 15 | 9 | 9 | 8 | 7 | 7 | 12 | 13 | 9 |
| 25 | | GRIP R | | 120 | ND | 86 | 107 | 123 | 121 | 112 | 98 | 51 | 85 | 148 |
| years old | | GRIP L | | 144 | | 87 | 143 | 167 | 141 | 139 | 136 | 94 | 111 | 119 |

ND = not done

TABLE 22

| PT # | LOT # | VISITS | | Baseline | 2 Wk | 3 Wk | 4 Wk | 5 Wk | 6 Wk | 26 Wk |
|---|---|---|---|---|---|---|---|---|---|---|
| patient #115 | Venom Fraction (1-2) | | | | | | | | | |
| B.F., | INDEX | PAIN | | 60/105 | 46/71 | 25/43 | 21/24 | 12/18 | 20/24 | 16/19 |
| Male; | | SWELLING | | 55/73 | 43/55 | 32/47 | 22/24 | 19/23 | 22/23 | 17/22 |
| cauc. | | SED RATE | | 60 | 68 | 80 | 86 | 80 | 84 | 75 |
| 61 years | | WALKING | | WC | | | | | | |
| old | | GRIP R | | 56 | 62 | 50 | 53 | 69 | 59 | 48 |
| | | GRIP L | | 66 | 68 | 60 | 82 | 89 | 69 | 49 |

WC = wheel chair

TABLE 23

| PT # | LOT # | VISITS | | Baseline | 2 Wk | 3 Wk | 4 Wk | 5 Wk | 6 Wk | 8 Wk | 10 Wk | 14 Wk | 18 Wk |
|---|---|---|---|---|---|---|---|---|---|---|---|---|---|
| patient #116 | Venom Fraction (2-1) | | | | | | | | | | | | |
| B.L., | INDEX | PAIN | | 22/28 | 9/11 | 8/12 | 12/14 | 9/9 | 11/13 | 8/10 | 7/7 | 8/9 | 9/9 |
| Fe- | | SWELLING | | 19/25 | 14/17 | 14/19 | 14/16 | 9/11 | 8/9 | 8/11 | 6/7 | 10/10 | 8/11 |
| male; | | SED RATE | | ND | 30 | ND | 40 | 50 | 51 | ND | 60 | ND | 41 |
| cauc. | | WALKING | | ND | 9 | 7 | 9 | 8 | 6 | 8 | 7 | 9 | 8 |
| 50 | | GRIP R | | 103 | 58 | 71 | 76 | 77 | 105 | 112 | 106 | 111 | 79 |
| years old | | GRIP L | | 82 | 61 | 73 | 68 | 89 | 86 | 70 | 73 | 72 | 91 |

ND = not done

TABLE 24

| PT # | LOT # | VISITS | | Baseline | 2 Wk | 3 Wk | 4 Wk | 5 Wk | 6 Wk | 8 Wk | 10 Wk | 14 Wk | 18 Wk |
|---|---|---|---|---|---|---|---|---|---|---|---|---|---|
| patient #117 | Venom Fraction (2-2) | | | | | | | | | | | | |
| E.R., | INDEX | PAIN | | 17/17 | 30/31 | 17/18 | 10/10 | 4/5 | 8/8 | 8/8 | 6/8 | 3/3 | 2/2 |
| Male; | | SWELLING | | 27/29 | 34/36 | 20/20 | 18/19 | 12/16 | 15/15 | 12/13 | 13/13 | 16/16 | 11/11 |
| black | | SED RATE | | 19 | 66 | 57 | 19 | ND | 37 | ND | 18 | ND | 42 |
| 67 | | WALKING | | ND | 11 | 12 | 11 | 11 | 10 | 9 | 11 | 10 | 11 |
| years | | GRIP R | | ND | 98 | 147 | 126 | 127 | 108 | 148 | 155 | 156 | 173 |
| old | | GRIP L | | | 130 | 166 | 162 | 154 | 160 | 160 | 168 | 182 | 173 |

ND = not done

TABLE 25

| PT # | LOT # | VISITS | | Baseline | 2 Wk | 3 Wk | 4 Wk | 5 Wk | 6 Wk | 8 Wk | 10 Wk | 14 Wk |
|---|---|---|---|---|---|---|---|---|---|---|---|---|
| patient #118 | Venom fraction (3-1) | | | | | | | | | | | |
| S.M., | INDEX | ⌈ PAIN | | 19/25 | 15/26 | 10/13 | 6/7 | 8/12 | 8/8 | 22/24 | 3/3 | 15/18 |
| Female; | | ⌊ SWELLING | | 16/22 | 13/22 | 11/16 | 9/14 | 11/16 | 10/15 | 15/19 | 6/8 | 17/21 |
| black | | SED RATE | | 33 | 10 | 41 | 45 | ND | ND | 64 | 37 | ND |
| 62 years | | WALKING | | 15 | 16 | 15 | 17 | 17 | 13 | 14 | 14 | 13 |
| old | | GRIP R | | 45 | 45 | 90 | 80 | 106 | 88 | 49 | 87 | 96 |
| | | GRIP L | | 40 | 68 | 90 | 76 | 70 | 110 | 44 | 88 | 144 |

ND = not done

TABLE 26

| PT # | LOT # | VISITS | | Baseline | 2 Wk | 3 Wk | 4 Wk | 5 Wk | 6 Wk | 7 Wk | 8 Wk |
|---|---|---|---|---|---|---|---|---|---|---|---|
| patient #119 | Venom Fraction (3-2) | | | | | | | | | | |
| J.W., | INDEX | ⌈ PAIN | | 9/9 | 14/14 | 22/22 | 19/19 | 11/15 | 14/14 | 22/25 | 5/5 |
| Female; | | ⌊ SWELLING | | 10/15 | 7/13 | 19/21 | 13/17 | 13/13 | 12/15 | 19/25 | 18/20 |
| black | | SED RATE | | 78 | ND | 76 | ND | 72 | 84 | ND | ND |
| 34 years | | WALKING | | 17 | 16 | 22 | 18 | 15 | 15 | 16 | 13 |
| old | | GRIP R | | 34 | 43 | 34 | 43 | 31 | 30 | 30 | 23 |
| | | GRIP L | | 23 | 26 | 26 | 31 | 25 | 28 | 27 | 31 |

ND = not done

TABLE 27

| PT # | LOT # | VISITS | | Baseline | 2 Wk | 3 Wk | 4 Wk | 5 Wk | 6 Wk | 7 Wk | 8 Wk |
|---|---|---|---|---|---|---|---|---|---|---|---|
| patient #120 | Venom Fraction (4-1) | | | | | | | | | | |
| B.H.., | INDEX | ⌈ PAIN | | 15/15 | 19/20 | 15/15 | 4/4 | 4/4 | 4/4 | 2/2 | 1/1 |
| Female; | | ⌊ SWELLING | | 8/8 | 14/15 | 6/6 | 13/13 | 9/9 | 8/8 | 9/9 | 2/2 |
| White | | SED RATE | | 60 | 95 | 72 | 81 | 70 | 80 | ND | 82 |
| 57 years | | WALKING | | 12 | 14 | 10 | 10 | 10 | 8 | 9 | 10 |
| old | | GRIP R | | 83 | 83 | 88 | 79 | 100 | 101 | 84 | 91 |
| | | GRIP L | | 77 | 70 | 74 | 73 | 73 | 76 | 71 | 73 |

ND = not done

TABLE 28

| PT # | LOT # | VISITS | | Baseline | 2 Wk | 3 Wk | 4 Wk | 5 Wk | 6 Wk | 7 Wk |
|---|---|---|---|---|---|---|---|---|---|---|
| patient #121 | Venom Fraction (4-2) | | | | | | | | | |
| R.K., | INDEX | ⌈ PAIN | | 25/26 | 19/19 | 20/20 | 29/34 | 31/32 | 15/16 | 18/19 |
| Female; | | ⌊ SWELLING | | 17/20 | 35/35 | 14/15 | 24/26 | 27/32 | 26/28 | 23/26 |
| white | | SED RATE | | 78 | 71 | 80 | 85 | 75 | 82 | ND |
| 57 years | | WALKING | | 23 | 20 | 25 | 30 | 28 | 32 | 32 |
| old | | GRIP R | | 107 | 120 | 84 | 73 | 73 | 91 | 84 |
| | | GRIP L | | 114 | 94 | 91 | 87 | 77 | 86 | 84 |

ND = not done

A review of these results show that at least three of the four patients receiving synthetic venom experienced a beneficial effect. If the late appearing beneficial effects in patient 119 are included then all four patients receiving synthetic venom responded positively.

A summary of the results observed, based on a physician and patient evaluation of the results, is provided in Table 29. These data support the conclusion that the synthetic venom is equivalent in activity to the natural venom.

TABLE 29

Results of 8 patients injected with natural or synthetic product.

| Patient Number | Material Injected[a] | Professional Evaluation[b] | Patient Evaluation | |
|---|---|---|---|---|
| 114 | 1-1 | + | ± | Natural |
| 115 | 1-2 | + | ± | Synthetic |
| 116 | 2-1 | + | ± | Synthetic |
| 117 | 2-2 | + | ± | Natural |
| 118 | 3-1 | + | + | Natural |
| 119 | 3-2 | − | + | Synthetic |
| 120 | 4-1 | + | + | Synthetic |

TABLE 29-continued

Results of 8 patients injected with natural or synthetic product.

| Patient Number | Material Injected[a] | Improvement Professional Evaluation[b] | Patient Evaluation | |
|---|---|---|---|---|
| 121 | 4-2 | — | — | Natural |

[a]Prepared and coded by Toyobo Co.
[b]Physician and nurse.

Example: Synthetic Ant Venom Components

In order to determine which of the components of the venom were necessary for its activity, synthetic compositions were created as outlined in Section 4.1.8, each of which eliminated one of the components of the natural ant venom. These were compared with the synthetic venom containing all the naturally-occurring components, for the ability to inhibit concanavalin-A induced proliferation of lymphocytes. The ability to inhibit this proliferation is indicative of immunosuppressive as well as anti-inflammatory activity.

Blood was obtained from individuals randomly selected from the transplantation program at University of Miami Medical School. Lymphocytes were separated from other blood cells by Ficoll-Hypaqune and centrifugation. Individual donor lymphocytes were used; populations were not pooled.

Lymphocytes were adjusted to $1 \times 10^6$/ml. One hundred μl of cells were added to each well on a microtiter plate. Two Con A mixtures were prepared, and 100 μl added per well, to a concentration of either 5 or 10 μg/treatment. The synthetic venom compositions were prepared, with components present in the same concentration as found in the natural venom, but with one of the natural components left out. Twenty-five μl of one of the ant venom solutions were added to each well. Synthetic ant venom containing all components was used as a control for each individual donor.

The plates were incubated for 5 days at 37° C., $CO_2$ atmosphere At this point, $^3$H-thymidine was added to each well. After 18 hours, the cells were harvested and counted in a scintillation counter to determine the rate of incorporation of the tritiated thymidine. Decreased inhibition by any of the component-deficient synthetic venoms was calculated as the average counts/ minute that are at least 50% higher than the average counts/minute of synthetic ant venom containing all components. The results are presented in Table 30.

TABLE 30

Inhibition of Concanavalin A (Con A)-induced transformation of human lymphocytes by compounds which comprise the synthetic ant venom.

| Compound Number | Compound Deleted From Mixture | Number of Lymphocyte Donors and (percent) Showing Decreased Inhibition of Con A-Induced Proliferation[b] | |
|---|---|---|---|
| | | 5 μg Con A | 10 μg/ml |
| 1 | Choline chloride[a] | 7/12[c] (58.3) | 8/11 (72.7) |
| 2 | Arginine | 9/12 (75.0) | 9/11 (81.8) |
| 3 | Putrescine | 6/12 (50.0) | 6/11 (54.5) |
| 4 | Ethanolamine | 3/12 (25.0) | 6/11 (54.5) |
| 5 | Ammonium chloride | 9/12 (75.0) | 11/11 (100.0) |
| 6 | Calcium chloride | 0/12 (0) | 4/11 (36.4) |
| 7 | Magnesium chloride | 2/12 (16.7) | 5/11 (45.4) |
| 8 | Lysine | 1/12 (8.3) | 3/11 (27.3) |

[a]Mixture of compounds 2-8 added to lymphocytes.
[b]Decreased inhibition: average counts/min that are at least 50% higher than average counts/min of synthetic ant venom control containing the compounds (1-8).
[c]Numerator: total no. of lymphocyte donors with decreased inhibition of Con A-induced proliferation. Denominator: total no. of lymphocyte donors with decreased inhibition by synthetic ant venom (compounds 1-8).

The results show the greatest loss of inhibition resulting from elimination of ammonium chloride followed closely by arginine and choline chloride. Elimination of putrescine or ethanolamine from the venom resulted in a significant but lesser decrease in inhibition. The absence of calcium chloride, magnesium chloride or lysine had relatively little effect on inhibiting activity of the venom, particularly at lower levels of Con A.

Methods of Treatment

In another aspect of the present invention and as demonstrated above in section 5.2 the anti-inflammatory, immunosuppressive and analgesic compound may be used to treat individuals afflicted with an autoimmune disease such as rheumatoid arthritis. Generally stated, the pharmaceutic composition utilized in this method of treatment comprises an anti-inflammatory, immunosuppressive and analgesic compound having an infrared absorption spectrum having characteristic absorption at about 3120 cm$^{-1}$, 3020 cm$^{-1}$, 1480 cm$^{-1}$ and 950 cm$^{-1}$ with no characteristic absorption at about 1640 cm$^{-1}$ and 1540 cm$^{-1}$ and a pharmaceutically acceptable carrier material.

The anti-inflammatory, immunosuppressive and analgesic compound is further characterized by the following:

(a) a negative strain test for a compound having high contents of glycoprotein, heparin, chondroitin sulfuric acid, polysaccharides and other hydrocarbons with periodic acid Schiff reagent (PAS);

(b) a negative color forming test result with anthrone reagent;

(c) a negative color forming test result for uronic acid by carbazole sulfate method;

(d) a negative adsorption test result for a compound having a mannose and glucose residue with Concanavalin A sepharose;

(e) a fractional molecular weight of less than about 1000 daltons; and (f) an inhibitory activity of normal human serum complement third component.

Generally stated, the method of treating an individual effected with an auto-immune disease comprises providing to said individual an effective amount of a pharmaceutical composition comprising an anti-inflammatory, immunosuppressive and analgesic compound having an infrared absorption spectrum having characteristic absorption at about 3120 cm$^{-1}$, 3020 cm$^{-1}$, 1660 cm$^{-1}$, 1480 cm$^{-1}$, 1400 cm$^{-1}$ and 950 cm$^{-1}$ with no characteristic absorption at about 1640 cm$^{-1}$ and 1540 cm$^{-1}$ and a pharmaceutically acceptable carrier material.

In a preferred treatment regime an effected individual would be provided with the above pharmaceutical composition for about 10 days although a medical professional may require either a significantly shorter (a few days) or longer (months or years) or even intermittent treatment regime depending on his professional evaluation of the patent response to this treatment. The above clinical results, however, significantly indicated that pain, inflammation and swelling is reduced for a period of at least about 1-4 weeks and up to 22 weeks and possibly even significantly longer in patients with an auto-immune disease after providing to them about 0.5 to 1.0 ml/day of the pharmaceutical composition for a period of about 10 days.

Since this compound is active in small amounts it is possible to provide it to an afflicted individual via a number of possible delivery systems. The pharmaceutical compositions may be provided in a form suitable for oral administration, i.e. in the form of tablets, capsules, solutions, lozenges, syrups, elixirs, suspensions, gels and powders. Preferably, it would be formulated so as to avoid breakdown by digestive fluids.

In addition, the anti-inflammatory, immuno-suppressive and analgesic compound may be provided, as above in the clinical examples, in a form suitable for parenteral administration. In this type of dosage form the active compound may be in either a solution or suspension.

It is also within the scope of this invention that the anti-inflammatory and analgesic compound be provided topically to an effected individual. In this type of dosage form the active compound may be formulated into an ointment, cream, paste, plater, powder, aerosol, lotion, transdermal patch and solution.

The ant venom extract hereof may be administered to subjects requiring treatment of any auto-immune condition. The aforementioned clinical trials involved treatment of rheumatoid arthritis. However, beneficial effects have also been observed in treatment of chronic active hepatitis and chronic asthma. The compositions of the present invention may also be used to treat other auto-immune conditions such as Sjogren's syndrome, systemic lupus erythematosus, and thyroid-related auto-immune diseases. Dosage, dose rate and method of administering may parallel that currently in use in clinical investigations of human derived materials, e.g. preferably for parenteral administration about 0.5-1.0 ml per day of the anti-inflammatory and analgesic compound of fraction 26 or fraction 41. However, it is also within the scope of this invention that the dosage could be significantly lower, i.e. about 0.01 ml per day to as high as about 10 ml per day, depending upon what amount a medical professional would view as the effective amount to treat an auto-immune disease afflicted individual. The dosage arrived at by the medical professional would depend upon the patients response, his experience with this compound and other auto-immune medicines with other patients along with a variety of other factors taken into consideration by him prior to rendering his professional evaluation.

As one example of an appropriate dosage in parenteral form 20 mg of fraction 26 or fraction 41 may be dissolved in 10 ml and the solution aseptically subdivided into individual vials, each suitable for parenteral administration. The vials are preferably stored at $-70°$ C. prior to use although they may also be stored at any temperature up to and including room temperature about $23°$ C.

The pharmaceutical compositions of the present invention can be formulated according to known methods to prepare pharmaceutically useful compositions, whereby the anti-inflammatory, immunosuppressive and analgesic compound hereof is combined in admixture with a pharmaceutically acceptable carrier vehicle. Suitable vehicles and their formulation are, for instance, described in Remington's Pharmaceutical Sciences by E. W. Martin, which is hereby incorporated by reference. Such compositions will contain an effective amount of the ant venom extract hereof together with a suitable amount of vehicle in order to prepare pharmaceutically acceptable compositions suitable for effective administration to the effected or diseased individual.

As an alternative to using the purified venom (fraction 26 or fraction 41) in therapy, it is possible to utilize synthetically prepared compositions. The preferred compositions comprise effective amounts of ammonium chloride and arginine, preferably in a concentration of at least about 1500-2500 $\mu g/ml$ for ammonium chloride and 1200-2200 $\mu g/ml$ for arginine. It is particularly preferred that the composition comprise, in addition, an effective amount of choline chloride, preferably in a concentration of at least about 2500-3500 $\mu g/ml$. In another preferred embodiment, the composition comprises, in addition to the aforementioned components, effective amounts of putrescine and ethanolamine, in respective concentrations of at least about 700-1700 $\mu g/ml$ and 500-1500 $\mu g/ml$. Although not essential, if it is desired to administer a composition identical to the natural purified fraction, calcium chloride, and/or magnesium chloride, and/or lysine may be added to the active components noted above. As these components are not critical the amounts are also not critical but may reflect their concentration in fraction 26, i.e., from about 50 up to about 100-200 $\mu g/ml$. The concentrations noted above are not to be considered limiting however, it will be understood by those skilled in the art that the amounts are provided for guidance, and may be varied to optimize results in accordance with the needs of a particular patient.

Administration of the synthetic venom is achieved in the same manner as described for natural venom.

While the anti-inflammatory, immunosuppressive and analgesic compounds have been characterized in detail, it is obvious that this invention is not to be considered as limited to the exact formulations or methods of treatment or production disclosed, and that changes in the formulations, methods of treatment or production may be made and still be within the spirit and scope of the invention.

We claim:

1. An aqueous composition comprising at least about 1,500 $\mu g/ml$ of ammonium chloride, at least about 1,200 $\mu g/ml$ of arginine, at least about 2,500 $\mu g/ml$ of choline chloride, at least about 700 $\mu g/ml$ of putrescine and at least about 500 $\mu g/ml$ of ethanolamine wherein said composition is capable of at least about 85% inactivation of C3 in normal human serum.

2. The aqueous composition of claim 1 which further comprises at least about 2,500 $\mu g/ml$ of choline chloride, at least about 700 $\mu g/ml$ of putrescine and at least about 500 $\mu g/ml$ of ethanolamine.

3. The aqueous composition of claim 2 which further comprises from about 50 $\mu g/ml$ to about 200 $\mu g/ml$ of calcium chloride, from about 50 $\mu g/ml$ to about 200 $\mu g/ml$ of magnesium chloride and from about 50 $\mu g/ml$ to about 200 $\mu g/ml$ of lysine.

4. A method for treating rheumatoid arthritis in animals which comprises administering to an animal in need of said treatment an effective amount of a composition comprising ammonium chloride and arginine wherein said composition is capable of at least about 85% inactivation of C3 in normal human serum and a pharmaceutically acceptable carrier.

5. The method of claim 4 wherein said composition is an aqueous composition and the concentration of ammonium chloride is at least about 1,500 µg/ml and the concentration of arginine is at least about 1,200 µg/ml.

6. The method of claim 5 wherein said composition further comprises a compound selected from the group consisting of at least about 2,500 µg/ml of choline chloride, at least about 700 µg/ml of putrescine and at least about 500 µg/ml of ethanolamine.

7. The method of claim 5 wherein said composition further comprises at least about 2,500 µg/ml of choline chloride, at least about 700 µg/ml of putrescine and at least about 500 µg/ml of ethanolamine.

8. The method of claim 7 wherein said composition further comprises from about 50 µg/ml to about 200 µg/ml of calcium chloride, from about 50 µg/ml to about 200 µg/ml of magnesium chloride and from about 50 µg/ml to about 200 µg/ml of lysine.

9. The method of claim 4 wherein said animal is a human.

* * * * *